(12) United States Patent
Christianson et al.

(10) Patent No.: US 11,617,645 B2
(45) Date of Patent: Apr. 4, 2023

(54) STRUCTURAL MEMBERS FOR PROSTHETIC MITRAL VALVES

(71) Applicant: Tendyne Holdings, Inc., St. Paul, MN (US)

(72) Inventors: Mark Christianson, Plymouth, MN (US); Chad Perrin, Andover, MN (US); Zachary Tegels, Minneapolis, MN (US); Craig Ekvall, East Bethel, MN (US); Robert M. Vidlund, Forest Lake, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 930 days.

(21) Appl. No.: 16/513,911

(22) Filed: Jul. 17, 2019

(65) Prior Publication Data
US 2019/0336282 A1  Nov. 7, 2019

Related U.S. Application Data

(63) Continuation of application No. 15/472,935, filed on Mar. 29, 2017, now Pat. No. 10,405,976, which is a
(Continued)

(51) Int. Cl.
*A61F 2/24* (2006.01)
*A61L 27/00* (2006.01)
(Continued)

(52) U.S. Cl.
CPC .......... *A61F 2/2418* (2013.01); *A61F 2/2409* (2013.01); *A61F 2/2415* (2013.01); *A61F 2/2457* (2013.01); *A61F 2210/0014* (2013.01); *A61F 2220/0016* (2013.01); *A61F 2220/0041* (2013.01); *A61F 2220/0075* (2013.01); *A61F 2220/0083* (2013.01); *A61F 2230/0019* (2013.01); *A61F 2230/0093* (2013.01);
(Continued)

(58) Field of Classification Search
CPC .... A61F 2/2418; A61F 2/2409; A61F 2/2415; A61F 2/2427
See application file for complete search history.

(56) References Cited

U.S. PATENT DOCUMENTS 2,697,008 A   12/1954 Ross
3,409,013 A   11/1968 Berry
(Continued)

FOREIGN PATENT DOCUMENTS

CN   1486161 A   3/2004
CN   1961845 A   5/2007
(Continued)

OTHER PUBLICATIONS

US 9,155,620 B2, 10/2015, Gross et al. (withdrawn)
(Continued)

*Primary Examiner* — William H Matthews
(74) *Attorney, Agent, or Firm* — Wei & Sleman LLP

(57) ABSTRACT

A self-expanding wire frame for a pre-configured compressible transcatheter prosthetic cardiovascular valve, a combined inner frame/outer frame support structure for a prosthetic valve, and methods for deploying such a valve for treatment of a patient in need thereof, are disclosed.

20 Claims, 16 Drawing Sheets

Related U.S. Application Data continuation of application No. 14/950,656, filed on Nov. 24, 2015, now Pat. No. 9,610,159, which is a continuation of application No. PCT/US2014/040188, filed on May 30, 2014, which is a continuation-in-part of application No. 14/155,417, filed on Jan. 15, 2014, now abandoned.

(60) Provisional application No. 61/829,076, filed on May 30, 2013.

(51) Int. Cl.
| | |
|---|---|
| A61L 27/06 | (2006.01) |
| A61L 27/14 | (2006.01) |
| A61L 27/34 | (2006.01) |
| A61L 27/36 | (2006.01) |
| A61L 27/54 | (2006.01) |
| A61L 33/00 | (2006.01) |
| A61L 27/50 | (2006.01) |

(52) U.S. Cl.
CPC ............ *A61F 2250/0039* (2013.01); *A61F 2250/0063* (2013.01); *A61F 2250/0098* (2013.01); *A61L 27/00* (2013.01); *A61L 27/06* (2013.01); *A61L 27/14* (2013.01); *A61L 27/34* (2013.01); *A61L 27/3629* (2013.01); *A61L 27/50* (2013.01); *A61L 27/54* (2013.01); *A61L 33/0011* (2013.01); *A61L 2300/236* (2013.01); *A61L 2400/16* (2013.01); *A61L 2430/20* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Fhuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |

(56) References Cited

U.S. PATENT DOCUMENTS

| | | |
|---|---|---|
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |

(56) References Cited

U.S. PATENT DOCUMENTS

| | | |
|---|---|---|
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0055606 A1 | 3/2004 | Hendricksen et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0096735 A1 | 5/2005 | Hojeibane et al. |

(56) References Cited

U.S. PATENT DOCUMENTS

| | | |
|---|---|---|
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |

(56) References Cited

U.S. PATENT DOCUMENTS

| | | |
|---|---|---|
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0054519 A1 | 3/2011 | Neuss |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0301703 A1 | 12/2011 | Glazier |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0021530 A1 | 1/2012 | Gellman |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0078347 A1 | 3/2012 | Braido et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1* | 8/2012 | Quadri ............... A61F 2/2427 623/2.18 |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |

(56) References Cited

U.S. PATENT DOCUMENTS

| | | | |
|---|---|---|---|
| 2015/0328001 A1 | 11/2015 | McLean | |
| 2015/0335424 A1 | 11/2015 | McLean | |
| 2015/0335429 A1 | 11/2015 | Morriss et al. | |
| 2015/0342717 A1 | 12/2015 | O'Donnell et al. | |
| 2015/0351903 A1 | 12/2015 | Morriss et al. | |
| 2015/0351906 A1 | 12/2015 | Hammer et al. | |
| 2016/0000562 A1 | 1/2016 | Siegel | |
| 2016/0008131 A1 | 1/2016 | Christianson et al. | |
| 2016/0067042 A1 | 3/2016 | Murad et al. | |
| 2016/0074160 A1 | 3/2016 | Christianson et al. | |
| 2016/0106537 A1 | 4/2016 | Christianson et al. | |
| 2016/0113764 A1 | 4/2016 | Sheahan | |
| 2016/0143736 A1 | 5/2016 | Vidlund | |
| 2016/0151155 A1 | 6/2016 | Lutter et al. | |
| 2016/0206280 A1 | 7/2016 | Vidlund et al. | |
| 2016/0242902 A1 | 8/2016 | Morriss | |
| 2016/0262879 A1 | 9/2016 | Meiri et al. | |
| 2016/0262881 A1 | 9/2016 | Schankereli et al. | |
| 2016/0278955 A1 | 9/2016 | Liu et al. | |
| 2016/0317290 A1 | 11/2016 | Chau | |
| 2016/0324635 A1 | 11/2016 | Vidlund et al. | |
| 2016/0346086 A1 | 12/2016 | Solem | |
| 2016/0367365 A1 | 12/2016 | Conklin | |
| 2016/0367367 A1 | 12/2016 | Maisano et al. | |
| 2016/0367368 A1 | 12/2016 | Vidlund et al. | |
| 2017/0079790 A1 | 3/2017 | Vidlund et al. | |
| 2017/0100248 A1 | 4/2017 | Tegels et al. | |
| 2017/0128208 A1 | 5/2017 | Christianson et al. | |
| 2017/0181854 A1 | 6/2017 | Christianson et al. | |
| 2017/0252153 A1 | 9/2017 | Chau et al. | |
| 2017/0266001 A1 | 9/2017 | Vidlund et al. | |
| 2017/0281343 A1 | 10/2017 | Christianson et al. | |
| 2017/0312076 A1 | 11/2017 | Lutter et al. | |
| 2017/0312077 A1 | 11/2017 | Vidlund et al. | |
| 2017/0319333 A1 | 11/2017 | Tegels et al. | |
| 2018/0028314 A1 | 2/2018 | Ekvall et al. | |
| 2018/0078368 A1 | 3/2018 | Vidlund et al. | |
| 2018/0078370 A1 | 3/2018 | Kovalsky et al. | |
| 2018/0147055 A1 | 5/2018 | Vidlund et al. | |
| 2018/0193138 A1 | 7/2018 | Vidlund | |
| 2018/0263618 A1 | 9/2018 | Vidlund et al. | |

FOREIGN PATENT DOCUMENTS

| | | | |
|---|---|---|---|
| CN | 2902226 Y | 5/2007 | |
| CN | 101146484 A | 3/2008 | |
| CN | 101180010 A | 5/2008 | |
| CN | 101180010 | 12/2010 | |
| CN | 101984938 A | 3/2011 | |
| CN | 102639179 A | 8/2012 | |
| CN | 102869317 A | 1/2013 | |
| CN | 102869318 A | 1/2013 | |
| CN | 102869321 A | 1/2013 | |
| CN | 103220993 A | 7/2013 | |
| CN | 102639179 B | 10/2014 | |
| DE | 2246526 A1 | 3/1973 | |
| DE | 19532846 A1 | 3/1997 | |
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049815 A1 | 4/2002 | |
| DE | 102006052564 B3 | 12/2007 | |
| DE | 102006052710 A1 | 5/2008 | |
| DE | 102007043830 A1 | 4/2009 | |
| DE | 102007043831 A1 | 4/2009 | |
| EP | 0103546 A1 | 3/1984 | |
| EP | 1057460 A1 | 12/2000 | |
| EP | 1088529 A2 | 4/2001 | |
| EP | 1469797 | 10/2004 | |
| EP | 1469797 B1 | 11/2005 | |
| EP | 2111800 A1 | 10/2009 | |
| EP | 2193762 A1 | 6/2010 | |
| EP | 2278944 A2 | 2/2011 | |
| EP | 2747707 A1 | 7/2014 | |
| EP | 2918248 A1 | 9/2015 | |
| FR | 2788217 A1 | 7/2000 | |
| FR | 2815844 A1 | 5/2002 | |
| JP | 2003505146 A | 2/2003 | |
| JP | 2005515836 A | 6/2005 | |
| JP | 2007509700 A | 4/2007 | |
| JP | 2008541863 A | 11/2008 | |
| JP | 2009514628 A | 4/2009 | |
| JP | 2009519783 A | 5/2009 | |
| JP | 2012504031 A | 2/2012 | |
| JP | 2012518465 A | 8/2012 | |
| JP | 2012519024 A | 8/2012 | |
| JP | 2013512765 A | 4/2013 | |
| NL | 1017275 C2 | 8/2002 | |
| SU | 1271508 A1 | 11/1986 | |
| WO | 9217118 A1 | 10/1992 | |
| WO | 9301768 A1 | 2/1993 | |
| WO | 9829057 A1 | 7/1998 | |
| WO | 9940964 A1 | 8/1999 | |
| WO | 9947075 A1 | 9/1999 | |
| WO | 2000018333 A1 | 4/2000 | |
| WO | 2000030550 A1 | 6/2000 | |
| WO | 200041652 A1 | 7/2000 | |
| WO | 200047139 A1 | 8/2000 | |
| WO | 2001035878 A2 | 5/2001 | |
| WO | 2001049213 A2 | 7/2001 | |
| WO | 2001054624 A1 | 8/2001 | |
| WO | 2001054625 A1 | 8/2001 | |
| WO | 2001056512 A1 | 8/2001 | |
| WO | 2001061289 A1 | 8/2001 | |
| WO | 0176510 A2 | 10/2001 | |
| WO | 200176510 A2 | 10/2001 | |
| WO | 0182840 | 11/2001 | |
| WO | 2001082840 A1 | 11/2001 | |
| WO | 2002004757 A1 | 1/2002 | |
| WO | 0222054 A1 | 3/2002 | |
| WO | 2002022054 A1 | 3/2002 | |
| WO | 2002028321 A2 | 4/2002 | |
| WO | 0236048 A1 | 5/2002 | |
| WO | 2002036048 A1 | 5/2002 | |
| WO | 2002041789 A2 | 5/2002 | |
| WO | 0243620 A1 | 6/2002 | |
| WO | 0249540 A2 | 6/2002 | |
| WO | 2002043620 A1 | 6/2002 | |
| WO | 2002049540 A2 | 6/2002 | |
| WO | 2002076348 A1 | 10/2002 | |
| WO | 2003003943 A2 | 1/2003 | |
| WO | 2003030776 A2 | 4/2003 | |
| WO | 2003047468 A1 | 6/2003 | |
| WO | 2003049619 A2 | 6/2003 | |
| WO | 2004019825 A1 | 3/2004 | |
| WO | 2005102181 A1 | 11/2005 | |
| WO | 2006014233 A2 | 2/2006 | |
| WO | 2006034008 A2 | 3/2006 | |
| WO | 2006064490 A1 | 6/2006 | |
| WO | 2006070372 A2 | 7/2006 | |
| WO | 2006105009 A1 | 10/2006 | |
| WO | 2006113906 A1 | 10/2006 | |
| WO | 2006127756 A2 | 11/2006 | |
| WO | 2007081412 A1 | 7/2007 | |
| WO | 2007100408 A2 | 9/2007 | |
| WO | 2008005405 A2 | 1/2008 | |
| WO | 2008035337 A2 | 3/2008 | |
| WO | 2008091515 A2 | 7/2008 | |
| WO | 2008125906 A2 | 10/2008 | |
| WO | 2008147964 A1 | 12/2008 | |
| WO | 2009024859 A2 | 2/2009 | |
| WO | 2009026563 A2 | 2/2009 | |
| WO | 2009045338 A1 | 4/2009 | |
| WO | 2009132187 A1 | 10/2009 | |
| WO | 2010090878 A2 | 8/2010 | |
| WO | 2010098857 A1 | 9/2010 | |
| WO | 2010121076 A2 | 10/2010 | |
| WO | 2011017440 A2 | 2/2011 | |
| WO | 2011022658 A1 | 2/2011 | |
| WO | 2011069048 A2 | 6/2011 | |
| WO | 2011072084 A2 | 6/2011 | |
| WO | 2011106735 A1 | 9/2011 | |

(56) References Cited

FOREIGN PATENT DOCUMENTS

| | | |
|---|---|---|
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013/028387 A2 | 2/2013 |
| WO | 2013045262 A1 | 4/2013 |
| WO | 2013059747 A1 | 4/2013 |
| WO | 2013028387 | 5/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

Japanese Office Action for Application No. 2020105100, dated Jun. 4, 2021, 4 pages.
A. P. Yoganathan et al., "The Current Status of Prosthetic Heart Valves, Polymetric Materials and Artificial Organs," American Chemical Society, Mar. 20, 1983 pp. 111-150.
Bernacca, G. M. et al., "Polyurethane heart valves: Fatigue failure, calcification, and polyurethane structure," Journal of Biomedical Materials Research, Mar. 5, 1997, 34(3):371-379.
Buckberg, G. et al., "Restoring Papillary Muscle Dimensions During Restoration in Dilated Hearts," Interactive Cardiovascular and Thoracic Surgery, 2005, 4:475-477.
Drawbaugh, K., "Feature—Heart Surgeons Explore Minimally Invasive Methods," Reuters Limited, Jul. 16, 1996, 3 pages.
Henning Rud Andersen, "Transluminal Catheter Implanted Prosthetic Heart Valves," International Journal of Angiology, 1998, Issue 2, vol. 7 pp. 102-106.
Moazami, N. et al., "Transluminal aortic valve placement: A feasibility study with a newly designed collapsible aortic valve," ASAIO Journal, Sep./Oct. 1996 42(5):M381-M385.
Rousseau, E. P. M. et al., "A mechanical analysis of the closed Hancock heart valve prosthesis," Journal of Biomechanics, 1988, 21(7):545-562.
Uchida, B. T. et al., "Modifications of Gianturco Expandable Wire Stents," Am. J. Roentgenol., May 1988, 150 (5):1185-1187.
US 9,155,620, 10/2015, Gross et al. (withdrawn)
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Third Office Action for Chinese Application No. 201480037269.5, dated Jun. 19, 2018, 8 pages.
Tofeig, M. et al., "Transcatheter Closure of a Mid-Muscular Ventricular Septal Defect with an Amplatzer VSD Occluder Device," Heart, 1999, 81:438-440.

Uchida, Barry T., et al., "Modifications of Gianturco Expandable Wire Stents," AJR:150, May 1988, Dec. 3, 1987, pp. 1185-1187.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.
"Shape Memory Alloys," Retrieved from the Internet: <http://webdocs.cs.ualberta.ca/~database/MEMS/sma.html>, Feb. 5, 2016, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Examination Report for European Application No. 14734333.9, dated Oct. 20, 2016, 6 pages.
Examination Report No. 1 for Australian Application No. 2014274056, dated Mar. 6, 2018, 4 pages.
Examination Report No. 2 for Australian Application No. 2014274056, dated May 9, 2018, 2 pages.
Extended European Search Report for European Application No. 18160595.7, dated Sep. 14, 2018, 7 pages.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.

(56) References Cited

OTHER PUBLICATIONS

Inoue, K. et al., "Clinical Application of Transvenous Mitral Commissurotomy by a New Balloon Catheter," The Journal of Thoracic and Cardiovascular Surgery, 1984, 87:394-402.

International Search Report and Written Opinion for International Application No. PCT/US2014/040188, dated Nov. 17, 2014, 12 pages.

Invitation to Pay Additional Fees and Partial International Search Report for International Application No. PCT/US2014/040188, dated Sep. 8, 2014, 5 pages.

Jin, X. Y. et al., "Aortic Root Geometry and Stentless Porcine Valve Competence," Seminars in Thoracic and Cardiovascular Surgery, Oct. 1999, 11(4):145-150.

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.

L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal of Artificial Organs, 1993, Issue 5, vol. 16, pp. 253-262.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, Georg, et al., Mitral valved stent implantation, European Journal of Cardio-Thoracic Surgery, 2010, vol. 38, pp. 350-355.

Ma, L. et al., "Double-crowned valved stents for off-pump mitral valve replacement," European Journal of Cardio-Thoracic Surgery, Aug. 2005, 28(2): 194-198.

Notice of Reasons for Rejection for Japanese Application No. 2016-517032, dated Feb. 13, 2018, 5 pages.

Office Action for Chinese Application No. 201480037269.5, dated Dec. 23, 2016.

Office Action for U.S. Appl. No. 14/950,656, dated Apr. 22, 2016, 5 pages.

Orton, C., "Mitralseal: Hybrid Transcatheter Mitral Valve Replacement," Symposium: Small Animal Proceedings, 2011, pp. 311-312.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W. et al., "Der Verschluβ des Ductus Arteriosus Persistens ohne Thorakotomie," Thoraxchirurgie Vaskuläre Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196( 11 ): 173-174.

Rashkind, W. J., "Historical Aspects of Interventional Cardiology: Past, Present, Future," Texas Heart Institute Journal, Dec. 1986, 13(4):363-367.

Reul, H. et al., "The Geomety of the Aortic Root in Health, at Valve Disease and After Valve Replacement," J. Biomechanics, 1990, 23(2):181-191.

Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.

Rosch, J. et al., "The Birth, Early Years and Future of Interventional Radiology," J Vasc Interv Radiol., Jul. 2003, 4:841-853.

Ross, D. N., "Aortic Valve Surgery," Guys Hospital, London, 1968, pp. 192-197.

Rousseau, E. P. M. et al., "A Mechanical Analysis of the Closed Hancock Heart Valve Prosthesis," Journal of Biomechanics, 1998, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Second Office Action for Chinese Application No. 201480037269.5, dated Nov. 6, 2017, 6 pages.

Selby, M.D., J. Bayne, "Experience with New Retrieval Forceps for Foreign Body Removal in the Vascular, Urinary, and Biliary Systems," Radiology 1990; 176:535-538.

\* cited by examiner

STRUCTURAL MEMBERS FOR PROSTHETIC MITRAL VALVES

CROSS-REFERENCE TO RELATED APPLICATIONS

This application is a continuation of U.S. patent application Ser. No. 15/472,935, filed on Mar. 29, 2017, which is a continuation of U.S. patent application Ser. No. 14/950,656, filed Nov. 24, 2015 and issued as U.S. Pat. No. 9,610,159 on Apr. 4, 2017, which is a continuation of International Application No. PCT/US2014/040188, filed May 30, 2014, which claims priority to and is a continuation-in-part of U.S. patent application Ser. No. 14/155,417, filed Jan. 15, 2014, which claims priority to and the benefit of U.S. Provisional Application No. 61/829,076, filed May 30, 2013. International Application No. PCT/US2014/040188 also claims priority to and the benefit of U.S. Provisional Application No. 61/829,076, filed May 30, 2013. Each of the foregoing disclosures is hereby incorporated by reference in its entirety.

BACKGROUND

Field of Invention

An improved transcatheter prosthetic heart valve includes structural members, such as in the form of wire frames, which provide support for the valve and aid in reducing or preventing leakage.

Background

Valvular heart disease and specifically aortic and mitral valve disease is a significant health issue in the US. Annually approximately 90,000 valve replacements are conducted in the US. Traditional valve replacement surgery, the orthotopic replacement of a heart valve, is an "open heart" surgical procedure. Briefly, the procedure necessitates a surgical opening of the thorax, initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure, largely due to the necessity for extra-corporeal circulation. Further, open heart surgery is often poorly tolerated in elderly patients.

Thus if the extra-corporeal component of the procedure could be eliminated, morbidities and cost of valve replacement therapies would be significantly reduced.

While replacement of the aortic valve in a transcatheter manner is the subject of intense investigation, lesser attention has been focused on the mitral valve. This is in part reflective of the greater level of complexity associated to the native mitral valve apparatus and thus a greater level of difficulty with regards to inserting and anchoring the replacement prosthesis.

Various problems exist in this field, including problems of insufficient articulation and sealing of the valve within the native annulus, pulmonary edema due to poor atrial drainage, perivalvular leaking around the installed prosthetic valve, lack of a good fit for the prosthetic valve within the native mitral annulus, atrial tissue erosion, excess wear on the valve structures, interference with the aorta at the posterior side of the mitral annulus, and lack of customization, to name a few. Accordingly, there is still a need for an improved prosthetic mitral valve.

SUMMARY

Apparatus, systems, and methods include a self-expanding wire frames for a prosthetic cardiovascular valve. The prosthetic cardiovascular valve includes a cylindrical framework defining a lumen. The cylindrical framework includes multiple generally diamond-shaped members. Each diamond-shaped member defines multiple lateral vertices and multiple longitudinal vertices. Each diamond-shaped member is coupled to one or more other diamond-shaped members. Each coupling can be at or about each of the lateral vertices of the diamond-shaped member.

DETAILED DESCRIPTION

Figure 1:
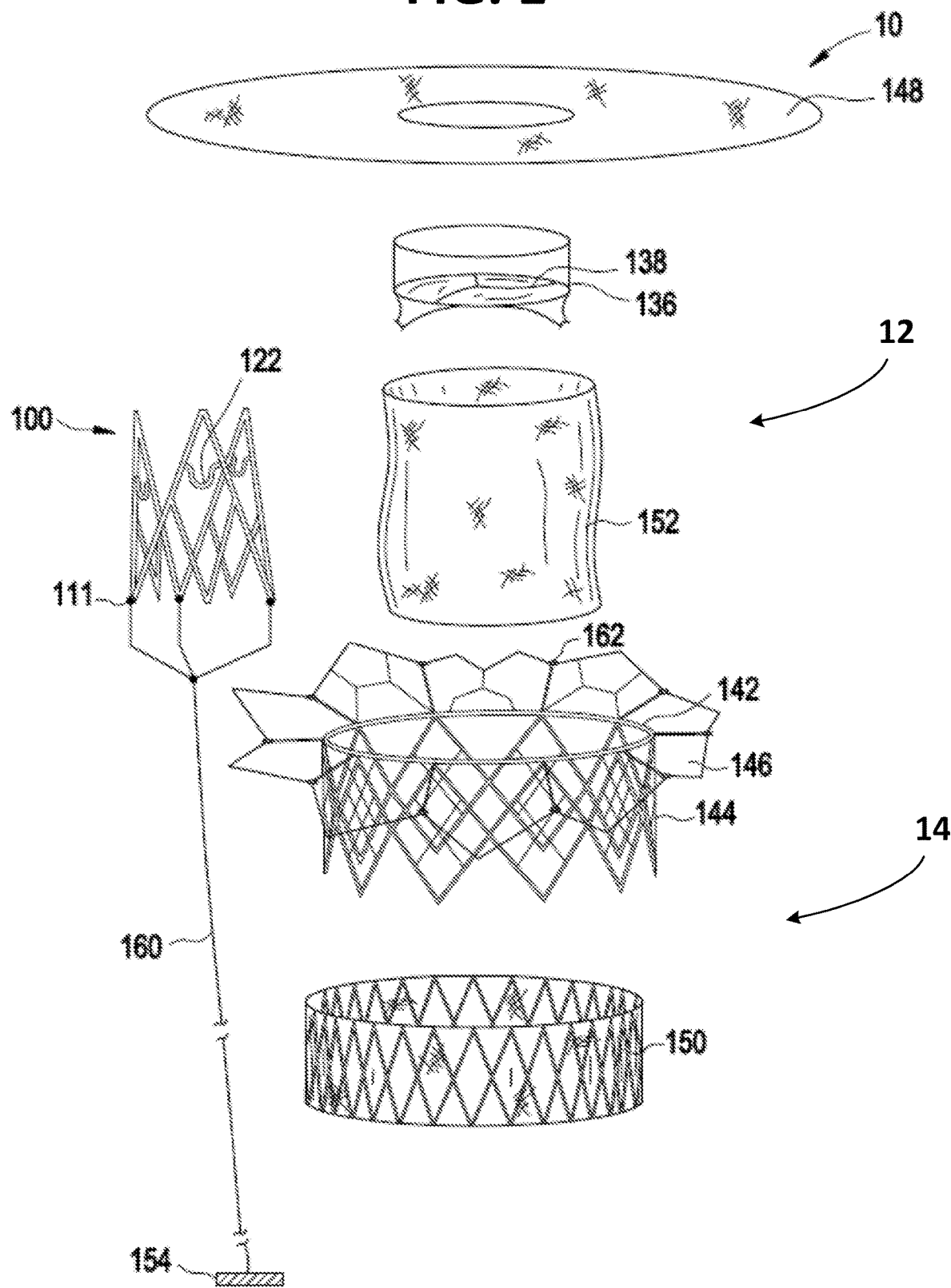
FIG. 1 is an exploded view of a prosthetic cardiovascular valve according to an embodiment.

FIG. 1 is an exploded view of one embodiment of a pre-configured compressible transcatheter prosthetic cardiovascular valve 10. In this embodiment, valve 10 includes an inner structure or assembly 12, and an outer structure or assembly 14. Valve 10 may be coupled to a tether 160, and a tether anchor 154.

Inner assembly 12 includes a self-expanding frame 100, an outer cylindrical wrap 152 disposed about the inner wire frame (to acts as a cover to prevent valvular leakage) and a leaflet structure 136 (comprised of articulating leaflets 138 that define a valve function). The leaflet structure 136 may be sewn to the inner wireframe 100. The wireframe 100 also has (tether) attachment apertures 111 to which the tether 160 can be attached. Tether 160 is connected to tether anchor 154, which in this embodiment is implemented as an epicardial securing pad.

Outer assembly 14 includes an outer stent or frame 144, an outer cover 150, and a cuff covering 148. In this embodiment, outer frame 144 has a flared, articulating collar or cuff 146 over which the cuff covering 148 is disposed. Cuff 146 has a D-shaped section 162 to accommodate and solve left ventricular outflow tract (LVOT) obstruction issues.

Cuff 146 may be configured a substantially flat plate that projects beyond the diameter of the tubular body of outer frame 144 to form a rim or border. The terms flared end, cuff, flange, collar, bonnet, apron, or skirting used interchangeable herein. When the tubular body of frame 144 is pulled through the aperture of a mitral valve aperture, the mitral annulus, such as by tether loops, in the direction of the left ventricle, the cuff acts as a collar to stop the frame from traveling any further through the mitral valve aperture. The entire prosthetic valve is held by longitudinal forces between the cuff, which is seated in the left atrium and mitral annulus, and the ventricular tethers attached to the left ventricle.

Cuff 146 may be formed from a stiff, flexible shape-memory material such as the nickel-titanium alloy material Nitinol® formed as wire, and covered by cuff covering 148, which may be formed of stabilized tissue or other suitable biocompatible or synthetic material. In one embodiment, the cuff is constructed from independent articulating radial tines or posts of wire extending axially around the circumference of the bend or seam where cuff 146 transitions to the tubular body of frame 144 (in an integral flared end or cuff) or where cuff 146 is attached to the frame body (in an implementation in which they are separate, but joined components).

With cuff cover 148 in place articulating radial tines or posts of wire provide the cuff the ability to move up and down, to articulate, along the longitudinal axis that runs through the center of frame 144. In other words, the individual articulating radial tines or posts of wire can independently move up and down, and can spring back to their original position due to the relative stiffness of the wire. The tissue or material that covers the cuff wire has a certain modulus of elasticity such that, when attached to the wire of the cuff, is able to allow the wire spindles to move. This flexibility gives the cuff, upon being deployed within a patient's heart, the ability to conform to the anatomical shape necessary for a particular application. In the example of a prosthetic mitral valve, the cuff is able to conform to the irregularities of the left atrium and shape of the mitral annulus, and to provide a tight seal against the atrial tissue adjacent the mitral annulus and the tissue within the mitral annulus. As stated previously, this feature provides a degree of flexibility in sizing the mitral valve and prevents blood from leaking around the implanted prosthetic heart valve.

An additional aspect of the cuff dimension and shape is that, when fully seated and secured, the edge of the cuff preferably should not be oriented laterally into the atrial wall, in which orientation it might produce a penetrating or cutting action on the atrial wall.

In some embodiments, the wire spindles of the cuff are substantially uniform in shape and size. In some embodiments, each loop or spindle may be of varying shapes and sizes. In this example, it is contemplated that the articulating radial tines or posts of wire may form a pattern of alternating large and small articulating radial tines or posts of wire, depending on where the valve is being deployed. In the case of a prosthetic mitral valve, pre-operative imaging may allow for customizing the structure of the cuff depending on a particular patient's anatomical geometry in the vicinity of the mitral annulus.

The cuff is constructed so as to provide sufficient structural integrity to withstand the intracardiac forces without collapsing.

Inner frame 100 and outer frame or frame 144, including cuff 146, are preferably formed to be deformed (compressed and/or expanded) and, when released, return to their original (undeformed) shapes. To achieve this, the components are preferably formed of materials, such as metals or plastics, that have shape memory properties. With regards to metals, Nitinol® has been found to be especially useful since it can be processed to be austenitic, martensitic or super elastic. Martensitic and super elastic alloys can be processed to demonstrate the required compression features. Thus, inner frame 100 and outer frame or frame 144, including cuff 145, are preferably constructed of Nitinol®, and are capable of maintaining their functions while under longitudinal forces that might cause a structural deformation or valve displacement. Other shape memory alloys, such as Cu—Zn—Al—Ni alloys, and Cu—Al—Ni alloys, may be used.

Inner frame 100 and outer frame or frame 144, including cuff 146, are preferably formed from a laser cut, thin-walled tube of Nitinol® The laser cuts form regular cutouts in the thin Nitinol® tube. Secondarily the tube is placed on a mold of the desired shape, heated to the martensitic temperature and quenched. The treatment of the frame in this manner will form a flared end or cuff that has shape memory properties and will readily revert to the memory shape at the calibrated temperature.

Alternatively, these components may be constructed from braided wire

The cuff provides several functions. The first function is to inhibit perivalvular leakage and regurgitation of blood around the prosthesis. By flexing and sealing across the irregular contours of the annulus and atrium, leakage is minimized or prevented.

The second function of the cuff is to provide an adjustable and/or compliant bioprosthetic valve. The heart and its structures undergo complex conformational changes during the cardiac cycle. For example, the mitral valve annulus has a complex geometric shape known as a hyperbolic paraboloid that is shaped like a saddle, with the horn being anterior, the seat back being posterior, and the left and right valleys located medially and laterally. Beyond this complexity, the area of the mitral annulus changes over the course of the cardiac cycle. Further, the geometry of the tricuspid valve and tricuspid annulus continues to be a topic of research, posing its own particular problems. Accordingly, compliance is a very important but unfortunately often overlooked requirement of cardiac devices. Compliance here refers to the ability of the valve to change conformation with the native annulus in order to maintain structural position and integrity throughout the cardiac cycle. Compliance with the motion of the heart is a particularly useful feature, especially the ability to provide localized compliance where the underlying surfaces are acting differently from the adjacent surfaces. This ability to vary throughout the cardiac cycle allows the valve to remain seated and properly deployed in a manner not heretofore provided.

Additionally, compliance may be achieved through the use of the tethers where the tethers are preferably made from an elastic material. Tether-based compliance may be used alone, or in combination with the cuff-based compliance.

The third function of the cuff is to enable the valve, during implantation surgery, to conform to the irregular surfaces of the atrium. This function can be enhanced by the use of independent tethers, allowing for side-to-side fitting of the valve within the annulus. For example, where three tethers are used, they can be spaced circumferentially about 120 degrees relative to each other, which allows the surgeon to observe whether or where perivalvular leaking might be occurring and to pull on one side or the other to create localized pressure and reduce or eliminate the leakage.

The fourth function of the cuff is to counter the forces that act to displace the prosthesis toward/into the ventricle (i.e. atrial pressure and flow-generated shear stress) during ventricular filling.

The heart is known to generate an average left atrial pressure between about 8 and 30 mm Hg (about 0.15 to 0.6 psi). This left atrial filling pressure is the expected approximate pressure that would be exerted in the direction of the left ventricle when the prosthesis is open against the outer face of the flared end or cuff as an anchoring force holding the flared end or cuff against the atrial tissue that is adjacent the mitral valve. Cuff 146 counteracts this longitudinal pressure against the prosthesis in the direction of the left ventricle to keep the valve from being displaced or slipping into the ventricle. In contrast, left ventricular systolic pressure, normally about 120 mm Hg, exerts a force on the closed prosthesis in the direction of the left atrium. The tethers counteract this force and are used to maintain the valve position and withstand the ventricular force during ventricular contraction or systole. Accordingly, cuff 146 has sufficient structural integrity to provide the necessary tension against the tethers without being dislodged and pulled into the left ventricle. After a period of time, changes in the geometry of the heart and/or fibrous adhesion between prosthesis and surrounding cardiac tissues may assist or replace the function of the ventricular tethers in resisting longitudinal forces on the valve prosthesis during ventricular contraction.

Additional features of the cuff include that it functions to strengthen the leaflet assembly/frame complex by providing additional structure. Further, during deployment, the cuff functions to guide the entire structure, the prosthetic valve, into place at the mitral annulus during deployment and to keep the valve in place once it is deployed. Another important function is to reduce pulmonary edema by improving atrial drainage.

The valve leaflets are held by, or within, a leaflet assembly. In some embodiments, the leaflet assembly comprises a leaflet wire support structure to which the leaflets are attached and the entire leaflet assembly is housed within the frame body. In this embodiment, the assembly is constructed of wire and stabilized tissue to form a suitable platform for attaching the leaflets. In this aspect, the wire and stabilized tissue allow for the leaflet structure to be compressed when the prosthetic valve is compressed within the deployment catheter, and to spring open into the proper functional shape when the prosthetic valve is opened during deployment. In this embodiment, the leaflet assembly may optionally be attached to and housed within a separate cylindrical liner made of stabilized tissue or material, and the liner is then attached to line the interior of the frame body.

In this embodiment, the leaflet wire support structure is constructed to have a collapsible/expandable geometry. In some embodiments, the structure is a single piece of wire. The wireform is, in one embodiment, constructed from a shape memory alloy such as Nitinol®. The structure may optionally be made of a plurality of wires, including between 2 to 10 wires. Further, the geometry of the wire form is without limitation, and may optionally be a series of parabolic inverted collapsible arches to mimic the saddle-like shape of the native annulus when the leaflets are attached. Alternatively, it may optionally be constructed as collapsible concentric rings, or other similar geometric forms, each of which is able to collapse or compress, then expand back to its functional shape. In some embodiments, there may be 2, 3 or 4 arches. In another embodiment, closed circular or ellipsoid structure designs are contemplated. In another embodiment, the wire form may be an umbrella-type structure, or other similar unfold-and-lock-open designs. In some embodiments utilizes super elastic Nitinol® wire approximately 0.015" in diameter. In this embodiment, the wire is wound around a shaping fixture in such a manner that 2-3 commissural posts are formed. The fixture containing the wrapped wire is placed in a muffle furnace at a predetermined temperature to set the shape of the wire form and to impart its super elastic properties. Secondarily, the loose ends of the wireform are joined with a stainless steel or Nitinol® tube and crimped to form a continuous shape. In some embodiments, the commissural posts of the wireform are adjoined at their tips by a circular connecting ring, or halo, whose purpose is to minimize inward deflection of the post(s).

In some embodiments, the leaflet assembly is constructed solely of stabilized tissue or other suitable material without a separate wire support structure. The leaflet assembly in this embodiment is also disposed within the lumen of the frame and is attached to the frame to provide a sealed joint between the leaflet assembly and the inner wall of the frame. By definition, it is contemplated within the scope of the invention that any structure made from stabilized tissue and/or wire(s) related to supporting the leaflets within the frame constitute a leaflet assembly. In this embodiment, stabilized tissue or suitable material may also optionally be used as a liner for the inner wall of the frame and is considered part of the leaflet assembly.

Liner tissue or biocompatible material may be processed to have the same or different mechanical qualities, such as thickness, durability, etc., from the leaflet tissue.

Multiple types of tissue and biocompatible material may be used to cover the cuff, to form the valve leaflets, to form a wireless leaflet assembly, and/or to line both the inner and/or outer lateral walls of outer frame 144. As stated previously, the leaflet component may be constructed solely from stabilized tissue, without using wire, to create a leaflet assembly and valve leaflets. In this aspect, the tissue-only leaflet component may be attached to the frame with or without the use of the wire form. In some embodiments, there can be anywhere from 1, 2, 3 or 4 leaflets, or valve cusps.

The tissue may be used to cover the inside of the frame body, the outside of the frame body, and the top and/or bottom side of the cuff wire form, or any combination thereof.

In some embodiments, the tissue used herein is optionally a biological tissue and may be a chemically stabilized valve of an animal, such as a pig. In some embodiments, the biological tissue is used to make leaflets that are sewn or attached to a metal frame. This tissue is chemically stabilized pericardial tissue of an animal, such as a cow (bovine pericardium) or sheep (ovine pericardium) or pig (porcine pericardium) or horse (equine pericardium).

Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old.

In some embodiments, the valve leaflets may optionally be made from a synthetic material such as polyurethane or polytetrafluoroethylene. Where a thin, durable synthetic material is contemplated, e.g. for covering the flared end or cuff, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethyleneglycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

In another embodiment, the valve leaflets may optionally have a surface that has been treated with (or reacted with) an anti-coagulant, such as, without limitation, immobilized heparin. Such currently available heparinized polymers are known and available to a person of ordinary skill in the art.

Alternatively, the valve leaflets may optionally be made from pericardial tissue or small intestine submucosal tissue.

In another embodiment, the prosthetic valve is sized and configured for use in areas other than the mitral annulus, including, without limitation, the tricuspid valve between the right atrium and right ventricle. Alternative embodiments may optionally include variations to the flared end or cuff structure to accommodate deployment to the pulmonary valve between the right ventricle and pulmonary artery, and the aortic valve between the left ventricle and the aorta. In one embodiment, the prosthetic valve is optionally used as a venous backflow valve for the venous system, including without limitation the vena cava, femoral, subclavian, pulmonary, hepatic, renal and cardiac. In this aspect, the flared end or cuff feature is utilized to provide additional protection against leaking.

As shown in FIG. 1, tether 160 may be attached to valve 10. Tether 160 (which may include multiple tethers) may extend to one or more tissue anchor locations within the heart. In some embodiments, the tether(s) extends downward through the left ventricle, exiting the left ventricle at the apex of the heart to be fastened on the epicardial surface outside of the heart. Similar anchoring is contemplated herein as it regards the tricuspid, or other valve structure requiring a prosthetic. There may be from 1 to 8, or more, tethers.

In some embodiments, the tether(s) may optionally be attached to the cuff to provide additional control over position, adjustment, and compliance. In some embodiments, one or more tethers are optionally attached to the cuff, in addition to, or optionally, in place of, the tethers attached to the outer frame 144. By attaching to the cuff and/or the frame, an even higher degree of control over positioning, adjustment, and compliance is provided to the operator during deployment.

During deployment, the operator is able to adjust or customize the tethers to the correct length for a particular patient's anatomy. The tether(s) also allows the operator to tighten the cuff onto the tissue around the valvular annulus by pulling the tether(s), which creates a leak-free seal.

In some embodiments, the tether(s) is optionally anchored to other tissue location(s) depending on the particular application of valve 10. In the case of a mitral valve, or the tricuspid valve, one or more tethers are optionally anchored to one or both papillary muscles, septum, and/or ventricular wall.

In some embodiments, the ventricular end of outer frame 144, or of inner frame 100, comes to 2-5 points onto which anchoring sutures or tether are affixed. The tethers will traverse the ventricle and ultimately be anchored to the epicardial surface of the heart approximately at the level of the apex. The tethers when installed under slight tension will serve to hold the valve in place, i.e. inhibit perivalvular leakage during systole.

The tethers, in conjunction with the cuff, provide greater compliance for the valve. The tethers may be made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. One or more of the tethers may optionally be elastic to provide an even further degree of compliance of the valve during the cardiac cycle. Upon being drawn to and through the apex of the heart, the tethers may be fastened by a suitable mechanism such as tying off to a pledget or similar adjustable button-type anchoring device to inhibit retraction of the tether back into the ventricle. It is also contemplated that the tethers might be bioresorbable/bioabsorbable and thereby provide temporary fixation until other types of fixation take hold such a biological fibrous adhesion between the tissues and prosthesis and/or radial compression from a reduction in the degree of heart chamber dilation.

Valve 10 may optionally be deployed with a combination of installation tethers and permanent tethers, attached to outer frame 144, and/or cuff 146, and/or inner frame 100, the installation tethers being removed after the valve is successfully deployed. It is also contemplated that combinations of inelastic and elastic tethers may optionally be used for deployment and to provide structural and positional compliance of the valve during the cardiac cycle.

Valve 10 may be deployed as a prosthetic mitral valve using catheter delivery techniques. The entire valve 10 is compressed within a narrow catheter and delivered to the annular region of the native valve, preferably the left atrium, with a pre-attached tether apparatus. There, the valve 10 is pushed out of the catheter where it springs open into its pre-formed functional shape without the need for manual expansion using an inner balloon catheter. When the valve 10 is pulled into place, the outer frame 144 is seated in the native mitral annulus, leaving the cuff 146 to engage the atrial floor and prevent pull-through (where the valve is pulled into the ventricle). The native leaflets are not cutaway as has been taught in prior prosthetic efforts, but are used to provide a tensioning and sealing function around the outer frame 144. The valve 10 is preferably deployed asymmetrically to address LVOT problems, unlike non-accommodating prosthetic valves that push against the A2 anterior segment of the mitral valve and close blood flow through the aorta, which anatomically sits immediately behind the A2 segment of the mitral annulus. Thus, D-shaped section 162 is preferably deployed immediately adjacent/contacting the A2 segment since the flattened D-shaped section 162 is structurally smaller and has a more vertical profile (closer to paralleling the longitudinal axis of the outer frame) and thereby exerts less pressure on the A2 segment. Once valve 10 is properly seated, tether 160 may be extended out through the apical region of the left ventricle and secured using an epicardial pad 154 or similar suture-locking attachment mechanism.

Valve 10 is, in one embodiment, apically delivered through the apex of the left ventricle of the heart using a catheter system. In one aspect of the apical delivery, the catheter system accesses the heart and pericardial space by intercostal delivery. In another delivery approach, the catheter system delivers valve 10 using either an antegrade or retrograde delivery approach using a flexible catheter system, and without requiring the rigid tube system commonly used. In another embodiment, the catheter system accesses the heart via a trans-septal approach.

In some embodiments, the frame body extends into the ventricle about to the edge of the open mitral valve leaflets (approximately 25% of the distance between the annulus and the ventricular apex). The open native leaflets lay against the outside frame wall and parallel to the long axis of the frame (i.e. the frame holds the native mitral valve open).

In some embodiments, the diameter should approximately match the diameter of the mitral annulus. Optionally, the valve may be positioned to sit in the mitral annulus at a slight angle directed away from the aortic valve such that it is not obstructing flow through the aortic valve. Optionally, the outflow portion (bottom) of the frame should not be too close to the lateral wall of the ventricle or papillary muscle as this position may interfere with flow through the prosthesis. As these options relate to the tricuspid, the position of the tricuspid valve may be very similar to that of the mitral valve.

In one embodiment, to control the potential tearing of tissue at the apical entry point of the delivery system, a circular, semi-circular, or multi-part pledget may be employed. The pledget may be constructed from a semi-rigid material such as PTFE felt. Prior to puncturing of the apex by the delivery system, the felt is firmly attached to the heart such that the apex is centrally located. Secondarily, the delivery system is introduced through the central area, or orifice as it may be, of the pledget. Positioned and attached in this manner, the pledget acts to control any potential tearing at the apex.

In another embodiment the valve can be seated within the valvular annulus through the use of tines or barbs. These may be used in conjunction with, or in place of one or more tethers. The tines or barbs are located to provide attachment to adjacent tissue. In some embodiments, the tines are optionally circumferentially located around the bend/transition area between frame body 144 and the cuff 146. Such tines are forced into the annular tissue by mechanical means such as using a balloon catheter. In one non-limiting embodiment, the tines may optionally be semi-circular hooks that upon expansion of the frame body, pierce, rotate into, and hold annular tissue securely.

Figure 2:
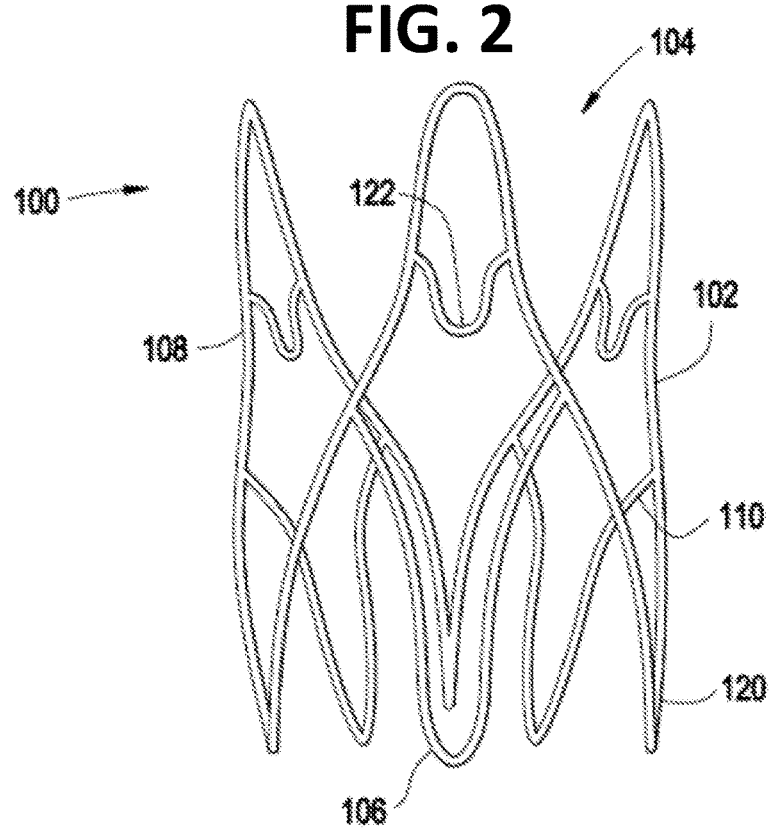
FIG. 2 is an oblique projection of a three-diamond self-expanding wire frame as a cylindrical frame defining a lumen according to an embodiment.

One embodiment of an inner frame 100 is shown in side view in FIG. 2. Frame 100 includes a cylindrical framework 102 defining a lumen 104, and including three generally diamond-shaped members 106, 108, 110. Each diamond-shaped member is directly connected to, or has at least one connecting member 120 connecting to, each of the other two diamond-shaped members. Spanning members 122 cross the open span of the diamond-shaped members and provide a strengthening structural enhancement, another sewing anchor location for the other components of inner assembly 12, or both.

Figure 3:
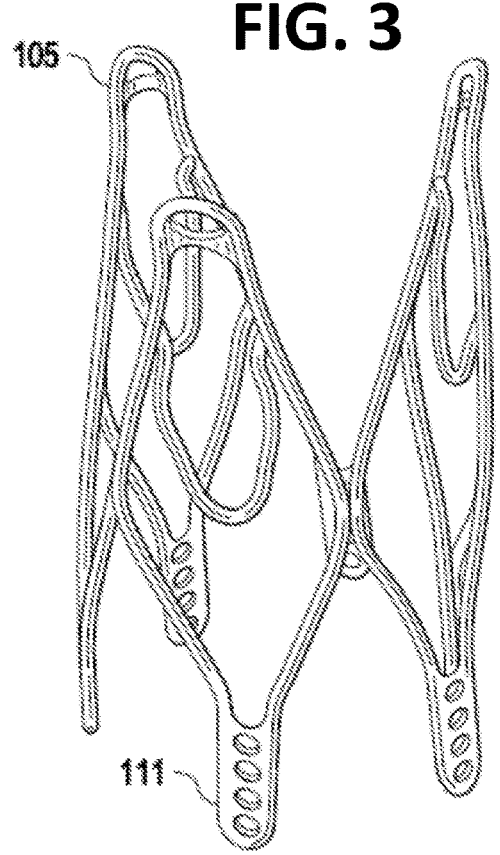
FIG. 3 is a perspective side view of a three-diamond self-expanding wire frame as a cylindrical frame defining a lumen according to another embodiment.

Another embodiment of inner frame 100 is shown in side view in FIG. 3. This embodiment includes optional valve sewing rings 105 and tether attachment structures 111. Each valve sewing ring 105 provides an aperture for sewing the leaflet tissue structures to the wire framework 100.

Figure 4:
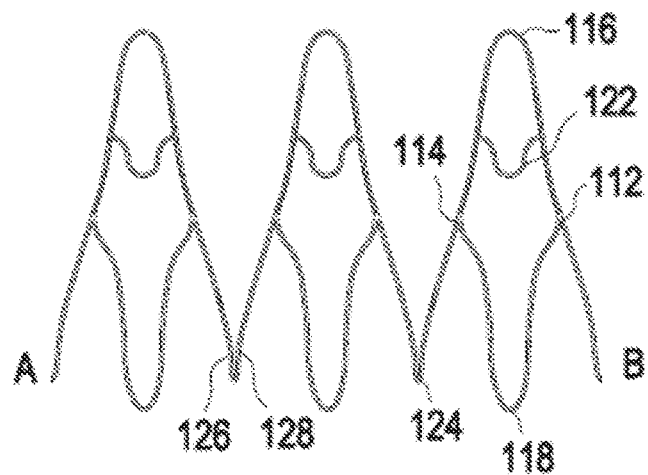
FIG. 4 is an opened and flattened view of a three-diamond cylindrical frame showing the detail of wire rods, multiple spanning rods, and vertices, according to another embodiment.

Another embodiment of inner frame 100 is shown in an opened and flattened view in FIG. 4. This view is intended primarily for illustrative purposes of the wireframe structure, since the manufacture of the cylindrical framework will generally be made from a laser-cut piece of Nitinol® tubing that is expanded to form a larger cylindrical structure, and the wireframe structure will generally not be manufactured from a rolled-up welded metal lattice. FIG. 4 shows each diamond-shaped member defining two lateral vertices 112 and 114 and two longitudinal vertices 116 and 118. Each diamond-shaped member is directly connected to, or has at least one connecting member 120 connecting to, each of the other two diamond-shaped members. The connecting members defined in this embodiment as joined legs 126, 128 connected at a V-shaped connecting vertex 124. FIG. 4 also shows spanning members 122 crossing the open span of the diamond-shaped members and providing a strengthening structural enhancement, another sewing anchor location, or both. FIG. 4 shows point A and point B, which are the locations at which the connecting members are joined to form a cylindrical structure (or said another way, the location at which the tubular inner frame 100 is cut to be opened up and flattened for the view shown in FIG. 4).

Figure 5:
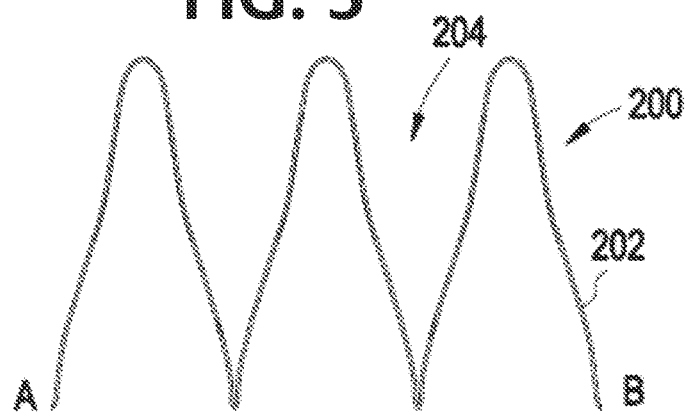
FIG. 5 is an opened and flattened view of an open-V cylindrical frame showing the detail of wire rods, and vertices, according to another embodiment.

Another embodiment of an inner frame, in this instance designated 200, is shown in FIG. 5 in a flattened view. Inner frame 200 includes a cylindrical framework 202 defining a lumen 204. As in FIG. 4, this view in FIG. 5 is intended primarily for illustrative purposes of the wireframe structure, and point A and point B designate the locations at which the wireframe is joined to form a cylindrical structure.

Figure 6:
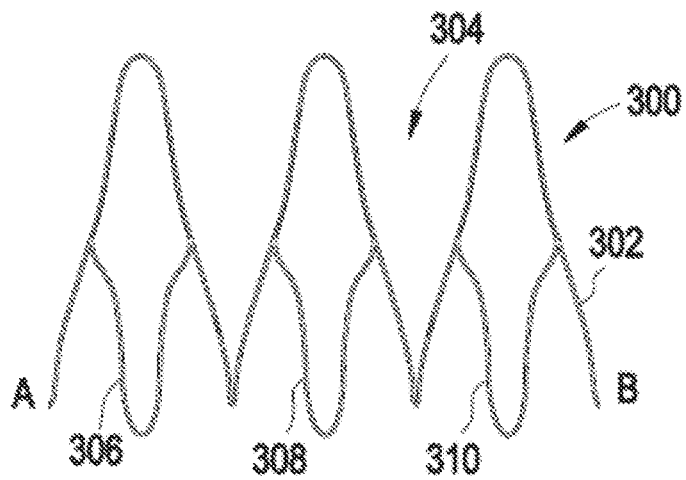
FIG. 6 is an opened and flattened view of a three-diamond cylindrical frame showing the detail of wire rods, spanning rods, and vertices, according to another embodiment.

Another embodiment of an inner frame, in this instance designated 300, is shown in flattened view in FIG. 6. Inner frame 300 includes three diamond-shaped members, not having spanning members. Cylindrical framework 302 defines a lumen 304 using each of diamond-shaped members 306, 308, and 310. FIG. 6 again shows point A and point B, which are the locations at which the connecting members are joined to form a cylindrical structure.

Figure 7:
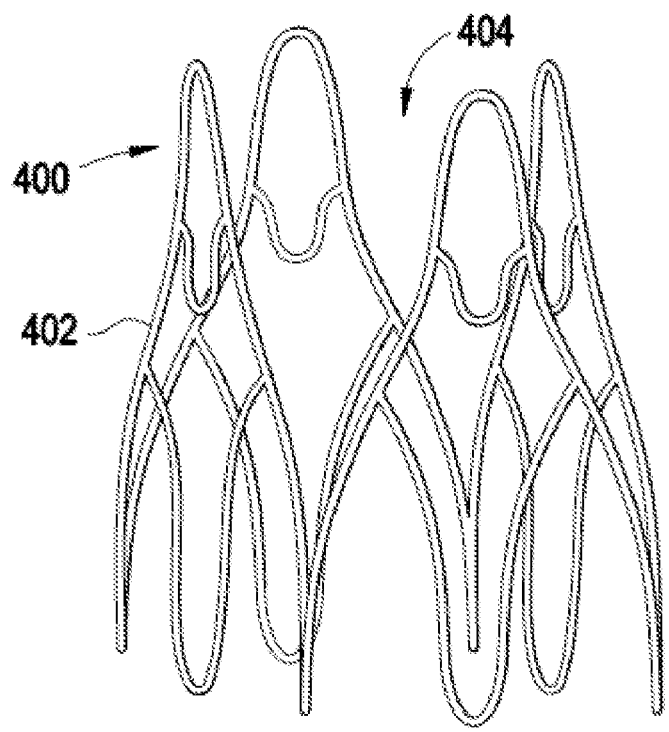
FIG. 7 is an oblique projection of a four-diamond self-expanding wire frame as a cylindrical frame defining a lumen, according to another embodiment.

Another embodiment of an inner frame, in this instance designated 400, is shown in side view in FIG. 7. This four-diamond embodiment includes a cylindrical framework 402 defining a lumen 404, in which cylindrical framework 402 includes four generally diamond-shaped members.

Figure 8:
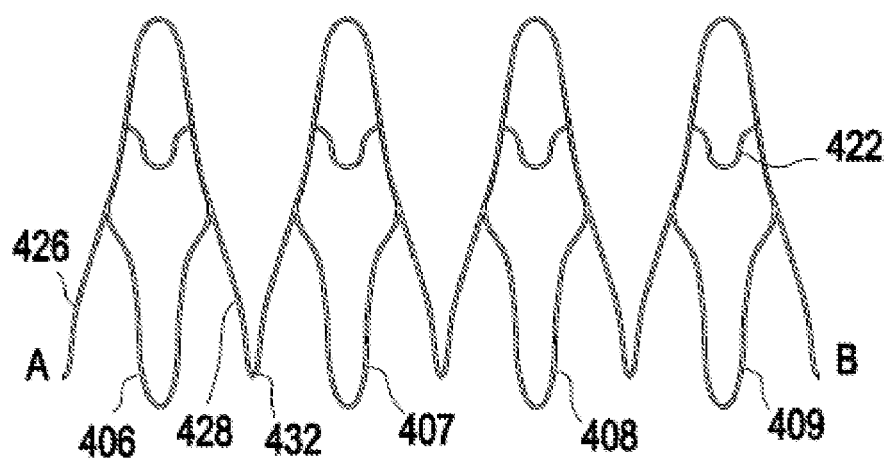
FIG. 8 is an opened and flattened view of a four-diamond cylindrical frame showing the detail of wire rods, multiple spanning rods, and vertices, according to another embodiment.

A flattened view of another four-diamond embodiment of inner frame 400 is shown in a flattened view in FIG. 8. FIG. 8 shows diamond-shaped members 406, 407, 408, and 409, each having joining legs, shown for 406 as joining components (legs) 426 and 428, which define vertices, such as that shown at joined end 432. FIG. 8 also shows spanning members, such as that shown at 422, crossing the open span of the diamond-shaped members and providing a strengthening structural enhancement, another sewing anchor location, or both. FIG. 8 again shows point A and point B, which are the locations at which the connecting members are joined to form a cylindrical structure.

Figure 9:
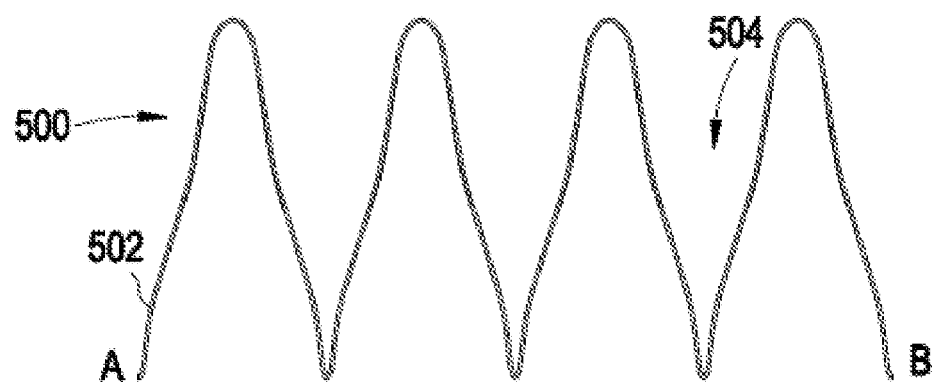
FIG. 9 is an opened and flattened view of an open-V cylindrical frame showing the detail of wire rods, and vertices, according to another embodiment.

Another embodiment of an inner frame, in this instance designated 500, is shown in flattened view in FIG. 9. Inner frame 500 includes cylindrical framework 502 defining lumen 504.

Figure 10:
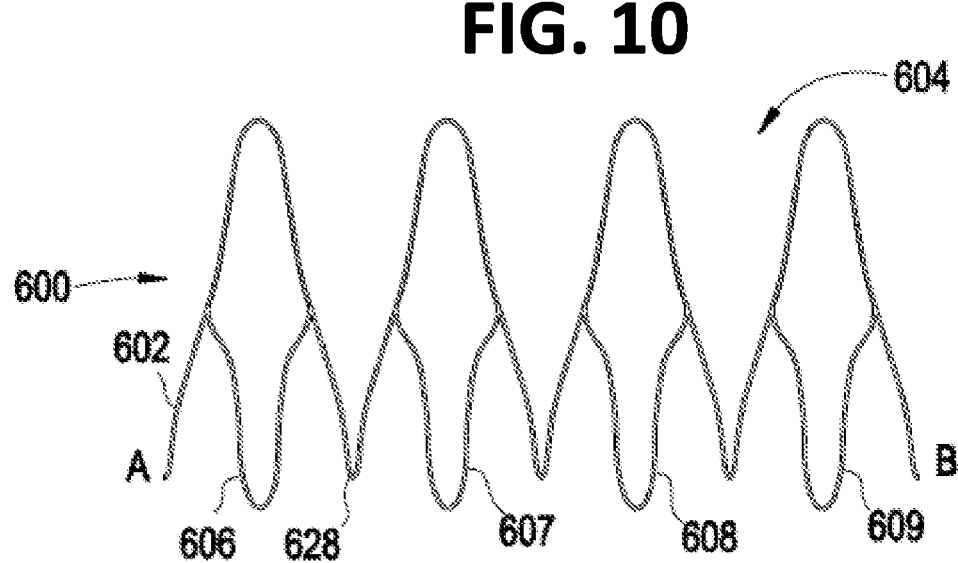
FIG. 10 is an opened and flattened view of a four-diamond cylindrical frame showing the detail of wire rods, spanning rods, and vertices, according to another embodiment.

Another embodiment of an inner frame, in this instance designated 600, is shown in flattened view in FIG. 10. Inner frame 600 includes cylindrical wireframe 602 defining a lumen 604 using diamond-shaped members 606, 607, 608, and 609. Each diamond-shaped member is joined at a connecting point, such as that shown at 628.

Figure 11:
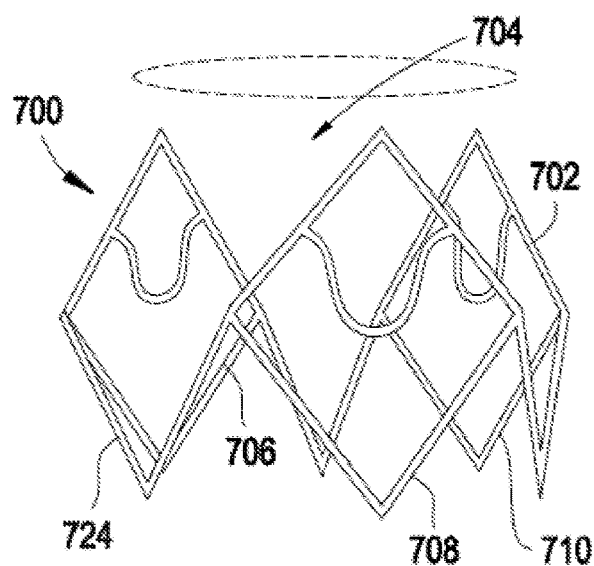
FIG. 11 is an oblique projection view of a three-square cylindrical frame showing the detail of wire rods, multiple spanning rods, and vertices, according to another embodiment.
Figure 12:
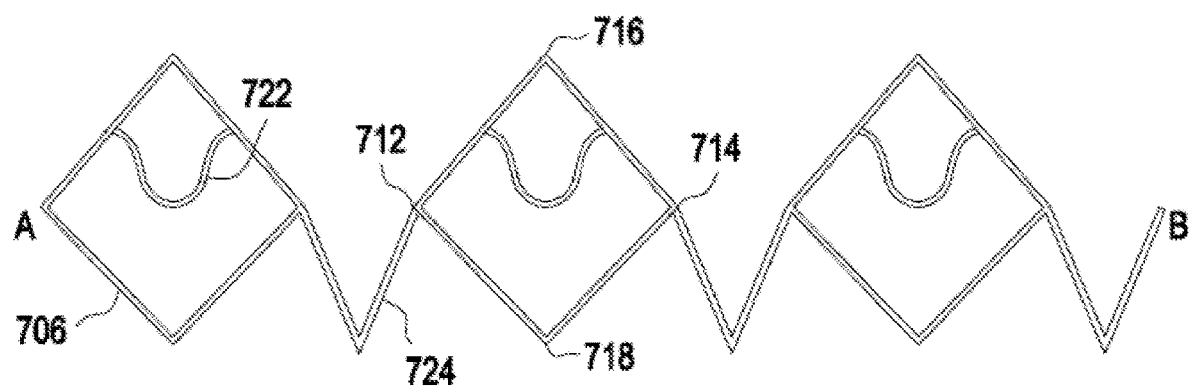
FIG. 12 is an opened and flattened view of the frame of FIG. 11.

Another embodiment of an inner frame, in this instance designated 700, is shown in side view in FIG. 11 and in flattened view in FIG. 12. This embodiment has three square-shaped members connected by a v-shaped joining element. Square-shaped members 706, 708, and 710, each have a v-shaped joining element, such as that shown as 724. Inner frame 700 also includes lateral vertices 712, 714 and longitudinal vertices 716, 718 and spanning members, such as that shown at 722, crossing the open span of the square-shaped members and providing a strengthening structural enhancement, another sewing anchor location, or both. Again, point A and point B are the locations at which the integral connecting members make their connection to form a cylindrical structure.

Figure 13:
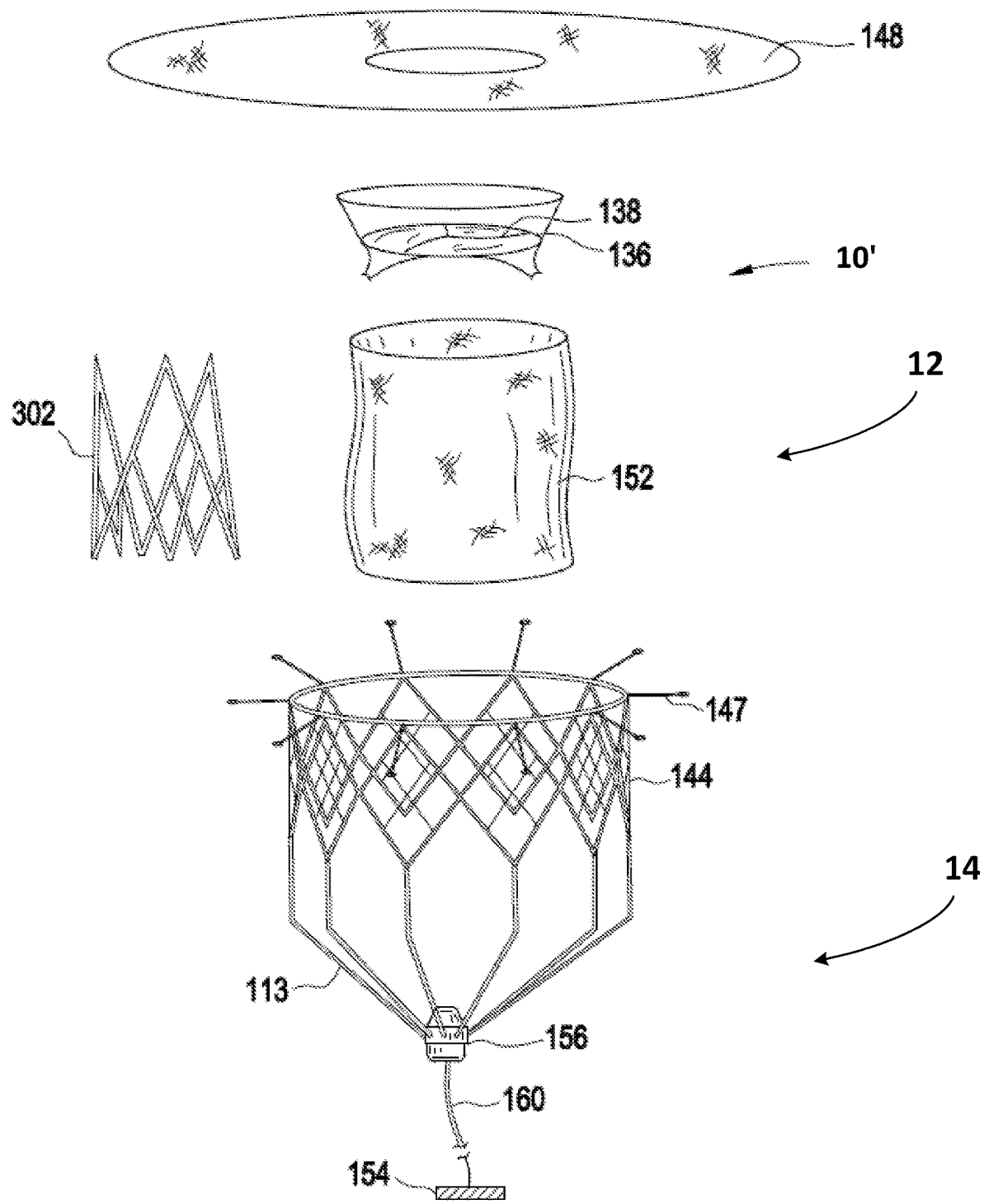
FIG. 13 is an exploded view of a prosthetic cardiovascular valve according to another embodiment.

Another embodiment of a prosthetic valve is shown in exploded view in FIG. 13. Valve 10' also includes an inner structure or assembly 12 and an outer structure or assembly 14. Valve 10' may also be coupled to a tether 160 and a tether anchor 154.

Inner assembly 12 includes inner frame 302, outer cylindrical wrap 152, and leaflet structure 136 (including articulating leaflets 138 that define a valve function). As in the embodiment in FIG. 1, leaflet structure 136 may be sewn to inner frame 302, and may use parts of inner frame 302 for this purpose. Inner assembly 12 is disposed within and secured within outer assembly 14.

Outer assembly 14 includes outer frame 144. Outer frame 144 may also have in various embodiments an outer frame cover of tissue or fabric (not pictured), or may be left without an outer cover to provide exposed wireframe to facilitate in-growth. Outer frame 144 has an articulating collar or cuff 147 is covered by cover 148 of tissue or fabric. Cuff 147 may also have in some embodiments a vertical A2 section to accommodate and solve left ventricular outflow tract (LVOT) obstruction issues.

In this embodiment, tether 160 is connected to valve 10' by outer frame 144, in contrast to the embodiment in FIG. 1, in which the tether is attached to valve 10 by inner frame 100. To implement this alternative tether attachment, in this embodiment, outer frame 144 also has attachment members or struts 113. A tether anchor 156 can be attached to the lower ends of the struts, and tether 160 can be attached to tether anchor 156. In this embodiment, tether 160 can be connected to epicardial securing pad 154.

Figure 14A:
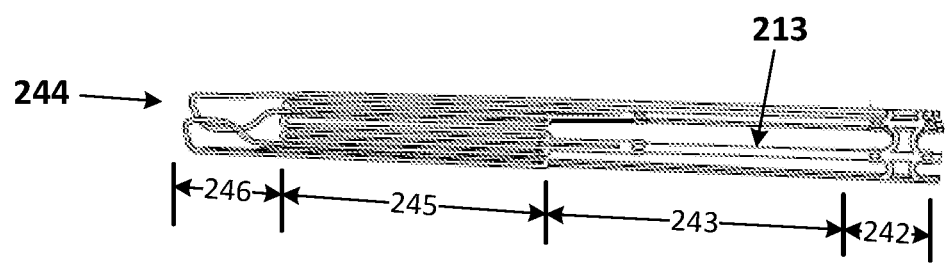
FIGS. 14A-14C show initial, partially expanded, and fully expanded states of an outer frame according to an embodiment.
Figure 14B:
Figure 14C:
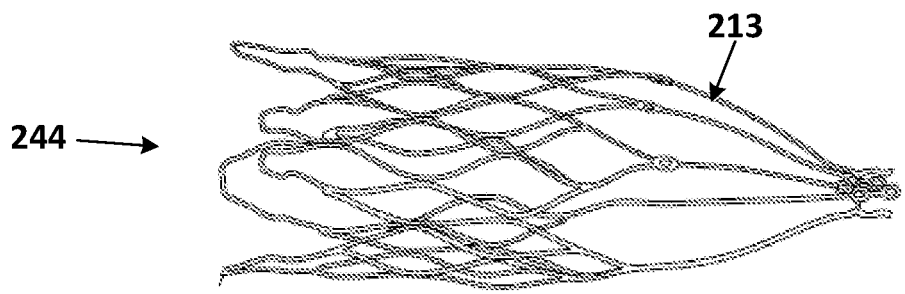

An embodiment of an outer frame 144 having attachment members or struts 113 is shown in FIGS. 14A to 14C. In this embodiment, outer frame 144 is formed from a milled or laser-cut tube of Nitinol®. FIG. 14A shows the tube as initially milled or laser cut, i.e. before deformation. The tube can be divided into four portions, corresponding to functionally different portions of the outer frame 144 in final form: cuff portion 246, frame body portion 245, strut portion 243, and tether connecting portion 242. Strut portion 243 includes six struts 213, which connect body portion 245 to tether clamp portion 242. Connecting portion 242 includes longitudinal extensions of struts 213, connected circumferentially by pairs of opposed, slightly V-shaped connecting members (or "micro-Vs"). Connecting portion 242 is configured to be radially collapsed by application of a compressive force, which causes the micro-Vs to become more deeply V-shaped, with the vertices moving closer together longitudinally and the open ends of the V shapes moving closer together circumferentially. In one embodiment, connecting portion 242 can be configured to compressively clamp or grip one end of a tether, either clamping directly onto a tether line (e.g. braided filament line) or onto an intermediate structure, such as a polymer or metal piece that is in term firmly fixed to the tether line. In another embodiment, connecting portion 242 can be coupled to a tether by a mechanical connection (e.g. stitches, pins, etc.), an adhesive connection, or any other suitable technique. In some embodiments, but clamping and one or more other connection techniques can be used in combination.

In contrast to connecting portion 242, cuff portion 246 and body portion 245 are configured to be expanded radially. Strut portion 243 forms a longitudinal connection, and radial transition, between the expanded body portion and the compressed connecting portion 242. FIG. 14B shows outer frame 244 in a partially deformed configuration, i.e. with connecting portion 242 compressed to a slightly smaller radial dimension than the initial configuration in FIG. 14A, and with cuff portion 246 and body portion 245 expanded to a slightly larger radial dimension. FIG. 14C shows outer frame 244 in a further partially deformed (though not fully deformed to the final, deployed configuration).

Figure 15:
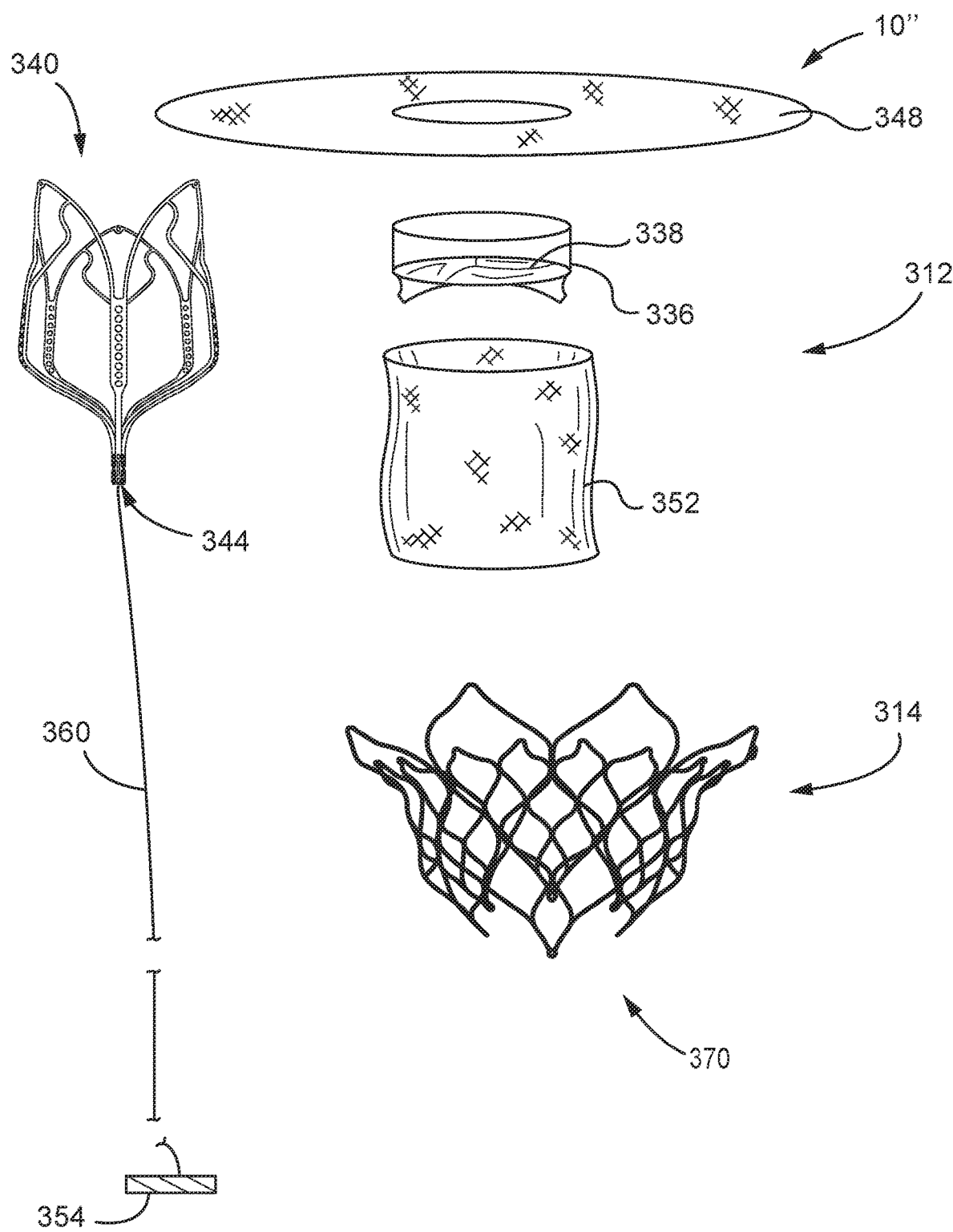
FIG. 15 is an exploded view of a prosthetic cardiovascular valve according to another embodiment.

Another embodiment of a prosthetic valve is shown in exploded view in FIG. 15. Valve 10" also includes an inner structure or assembly 312 and an outer structure or assembly 314. Valve 10" may also be coupled to a tether 360 and a tether anchor 354.

Inner assembly 312 includes inner frame 340, outer cylindrical wrap 352, and leaflet structure 336 (including articulating leaflets 338 that define a valve function). As in the embodiment in FIGS. 1 and 13, leaflet structure 336 may be sewn to inner frame 340, and may use parts of inner frame 340 for this purpose. Inner assembly 312 is disposed within and secured within outer assembly 314, as described in more detail below.

Outer assembly 314 includes outer frame 370. Outer frame 370 may also have in various embodiments an outer frame cover of tissue or fabric (not pictured), or may be left without an outer cover to provide exposed wireframe to facilitate in-growth. Outer frame 370 may also have an articulating collar or cuff 347 covered by cover 348 of tissue or fabric.

In this embodiment, tether 360 is connected to valve 10" by inner frame 340, similar to the embodiment in FIG. 1, but employing the connecting portion and strut portion features of the outer frame 144 of the valve 10' in FIG. 13. Thus, inner frame 340 includes tether connecting or clamping portion 344 by which inner frame 340, and by extension valve 10", is coupled to tether 360.

Figure 16:
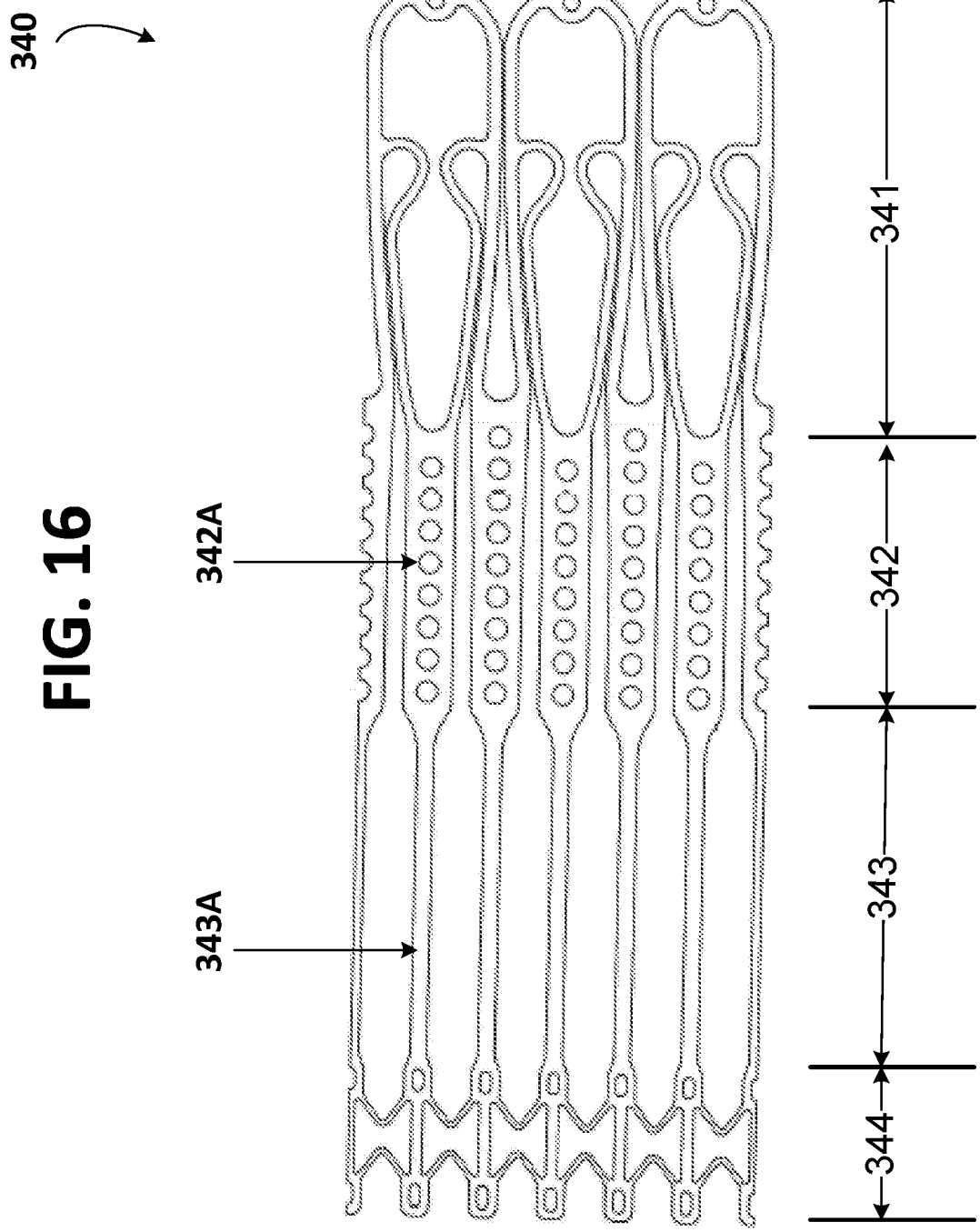
FIG. 16 is an opened and flattened view of an unexpanded inner wireframe structure, according to an embodiment.
Figure 17:
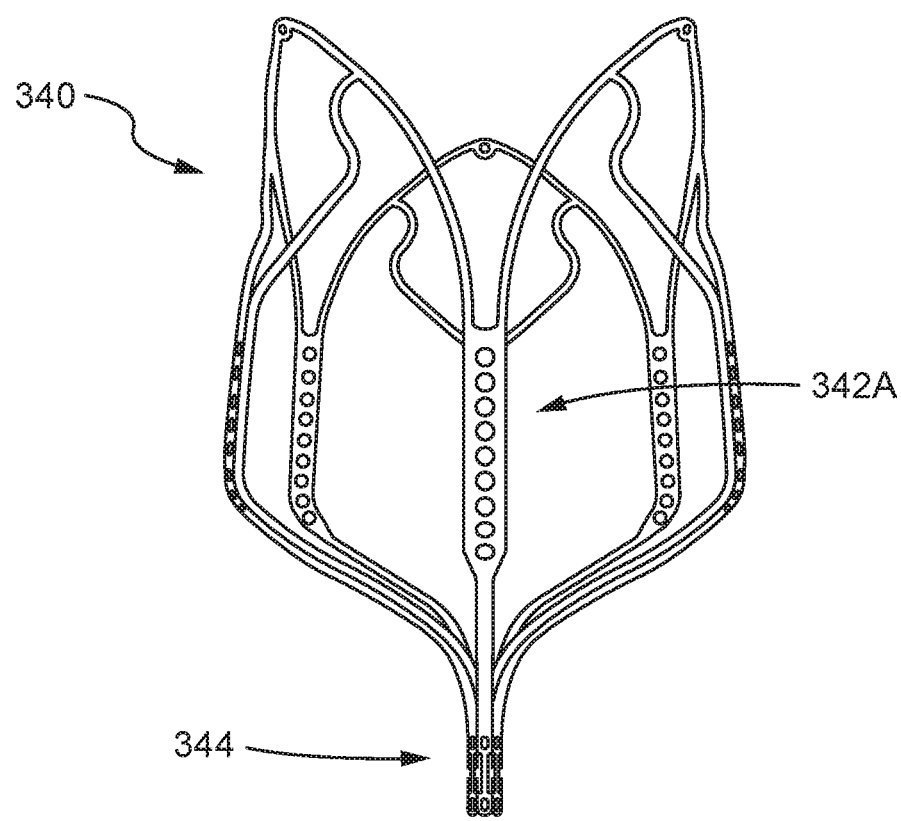
FIGS. 17 and 18 are side and bottom views, respectively, of the inner wireframe structure of FIG. 16 in an expanded configuration.
Figure 18:
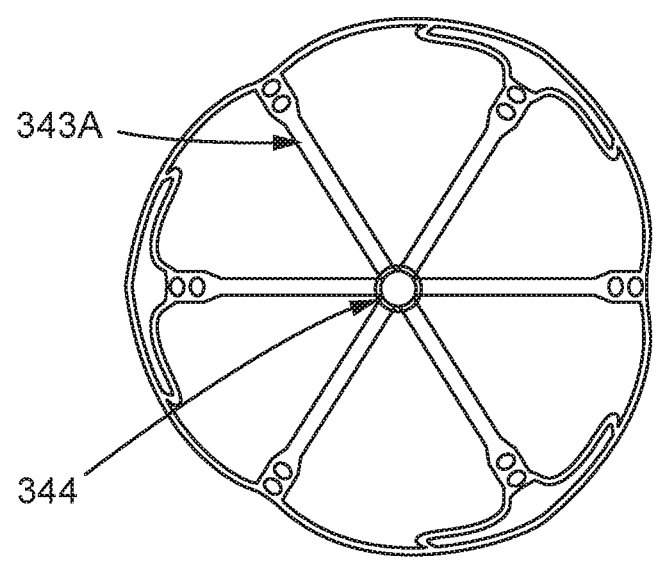

Inner frame 340 is shown in more detail in FIGS. 16-18. Inner frame 340 can be formed from a milled or laser-cut tube of, for example, Nitinol®. Inner frame 340 is illustrated in FIG. 16 in an undeformed, initial state, i.e. as milled or laser-cut, but cut and unrolled into a flat sheet for ease of illustration. Inner frame 340 can be divided into four portions, corresponding to functionally different portions of the inner frame 340 in final form: apex portion 341, body portion 342, strut portion 343, and tether clamp portion 344. Strut portion 343 includes six struts, such as strut 343A, which connect body portion 342 to tether clamp portion 344.

Connecting portion 344 includes longitudinal extensions of the struts, connected circumferentially by pairs of micro-V's. Similar to connecting portion 242 of outer frame 244 in FIGS. 14A-C, connecting portion 344 is configured to be radially collapsed by application of a compressive force, which causes the micro-Vs to become more deeply V-shaped, with the vertices moving closer together longitudinally and the open ends of the V shapes moving closer together circumferentially. Thus, connecting portion 344 can clamp or grip one end of a tether, either connecting directly onto a tether line (e.g. braided filament line) or onto an intermediate structure, such as a polymer or metal piece that is in term firmly fixed to the tether line. Other techniques can be used to connect a tether to connection portion 344, as discussed above for connection portion 242 of outer frame 244.

In contrast to connecting portion 344, apex portion 341 and body portion 342 are configured to be expanded radially. Strut portion 343 forms a longitudinal connection, and radial transition, between the expanded body portion and the compressed connecting portion 344.

Body portion 342 includes six longitudinal posts, such as post 342A. The posts can be used to attach leaflet structure 336 to inner frame 340, and/or can be used to attach inner assembly 312 to outer assembly 314, such as by connecting inner frame 340 to outer frame 370. In the illustrated embodiment, the posts include openings through which connecting members (such as suture filaments and/or wires) can be passed to couple the posts to other structures.

Inner frame 340 is shown in a fully deformed, i.e. to the final, deployed configuration, in side view and bottom view in FIGS. 17 and 18, respectively.

Figure 19:
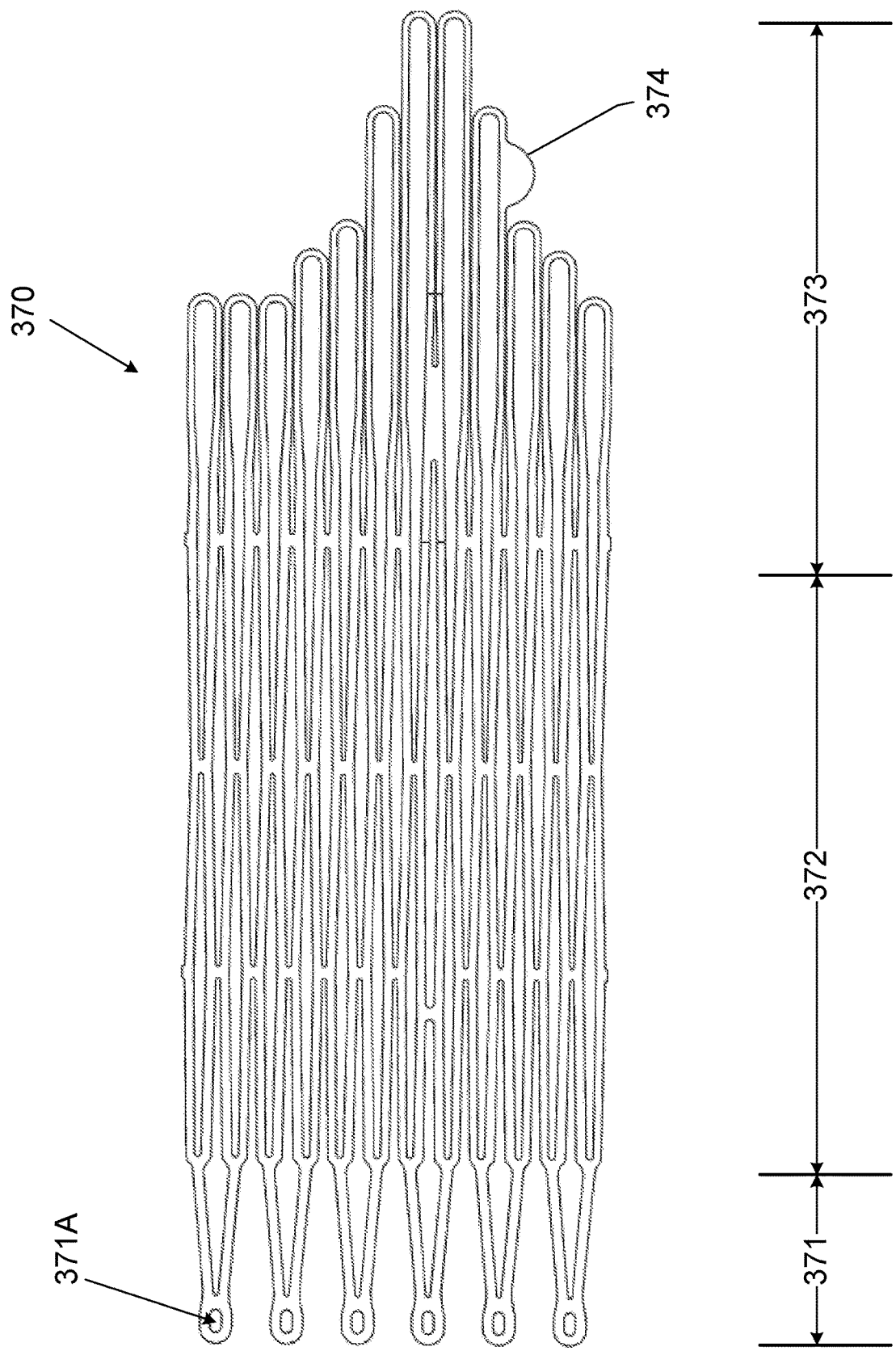
FIG. 19 is an opened and flattened view of an unexpanded outer frame according to an embodiment.
Figure 20:
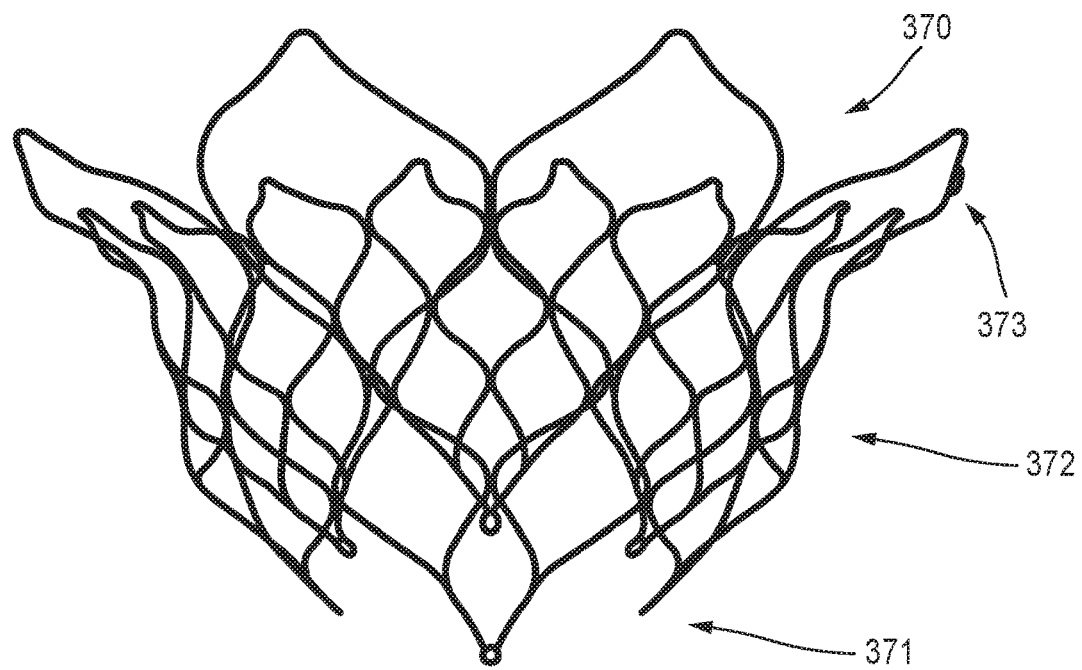
FIGS. 20 and 21 are side and top views, respectively, of the outer frame of FIG. 19 in an expanded configuration.
Figure 21:
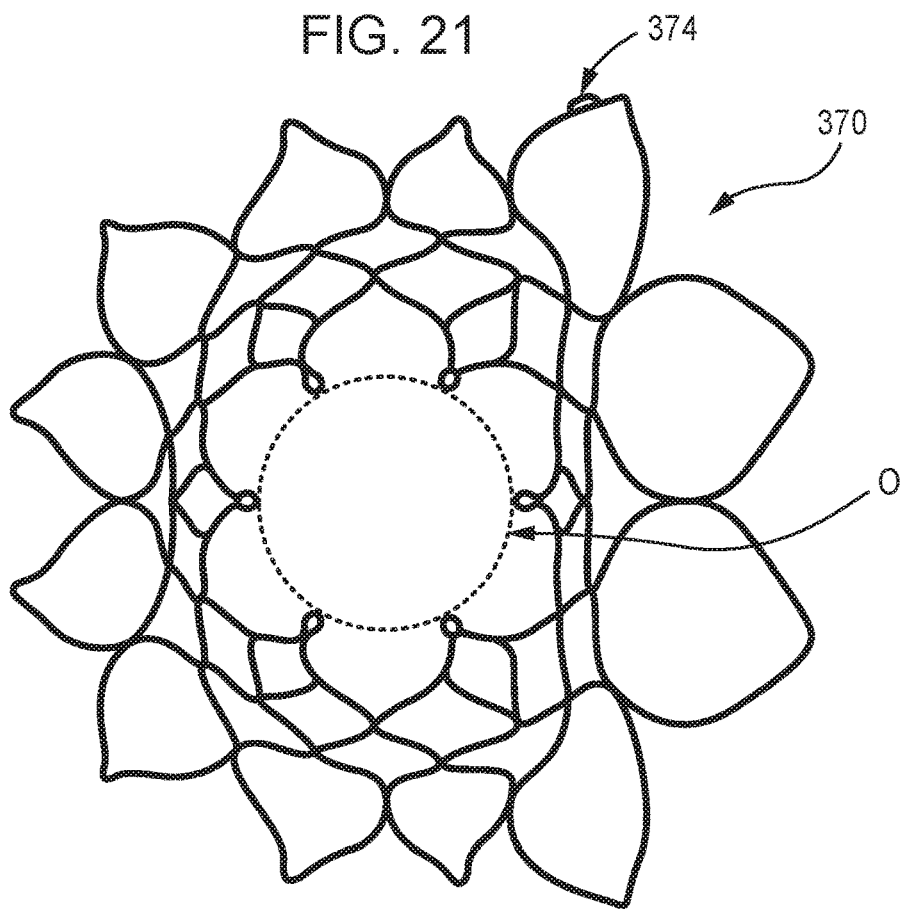

Outer frame 370 of valve 10" is shown in more detail in FIGS. 19-21. Outer frame 370 can be formed from a milled or laser-cut tube of, for example, Nitinol®. Outer frame 370 is illustrated in FIG. 19 in an undeformed, initial state, i.e. as milled or laser-cut, but cut and unrolled into a flat sheet for ease of illustration. Outer frame 370 can be similar to outer frame 144 described above in connection with valves 10 and 10'. Outer frame 370 can be divided into a coupling portion 371, a body portion 372, and a cuff portion 373, as shown in FIG. 19.

Coupling portion 371 includes multiple openings or apertures, such as 371A, by which outer frame 370 can be coupled to inner frame 340, as discussed in more detail below.

In this embodiment, cuff portion 373 includes an indicator 374. In this embodiment, indicator 374 is simply a broader portion of the wire frame element of cuff portion 373, i.e. Indicator 374 is more apparent on radiographic or other imaging modalities than the surrounding wire frame elements of cuff portion 373. In other embodiments, indicator 374 can be any distinguishable feature (e.g., protrusion, notch, etc.) and/or indicia (e.g., lines, markings, tic marks, etc.) that enhance the visibility of the part of cuff portion 373 on which it is formed, or to which it is attached. Indicator 374 can facilitate the implantation of the prosthetic valve by providing a reference point or landmark that the operator can use to orient and/or position the valve (or any portion of the valve) with respect to the native valve or other heart structure. For example, during implantation, an operator can identify (e.g., using echocardiography) the indicator 373 when the valve is situated in a patient's heart. The operator can therefore determine the location and/or orientation of the valve and make adjustments accordingly.

Outer frame 370 is shown in a fully deformed, i.e. to the final, deployed configuration, in side view and top view in FIGS. 20 and 21, respectively. As best seen in FIG. 21, the lower end of coupling portion 371 forms a roughly circular opening (identified by "O" in FIG. 21). The diameter of this opening preferably corresponds approximately to the diameter of body portion 342 of inner frame 340, to facilitate coupling of the two components of valve 10".

Figure 22:
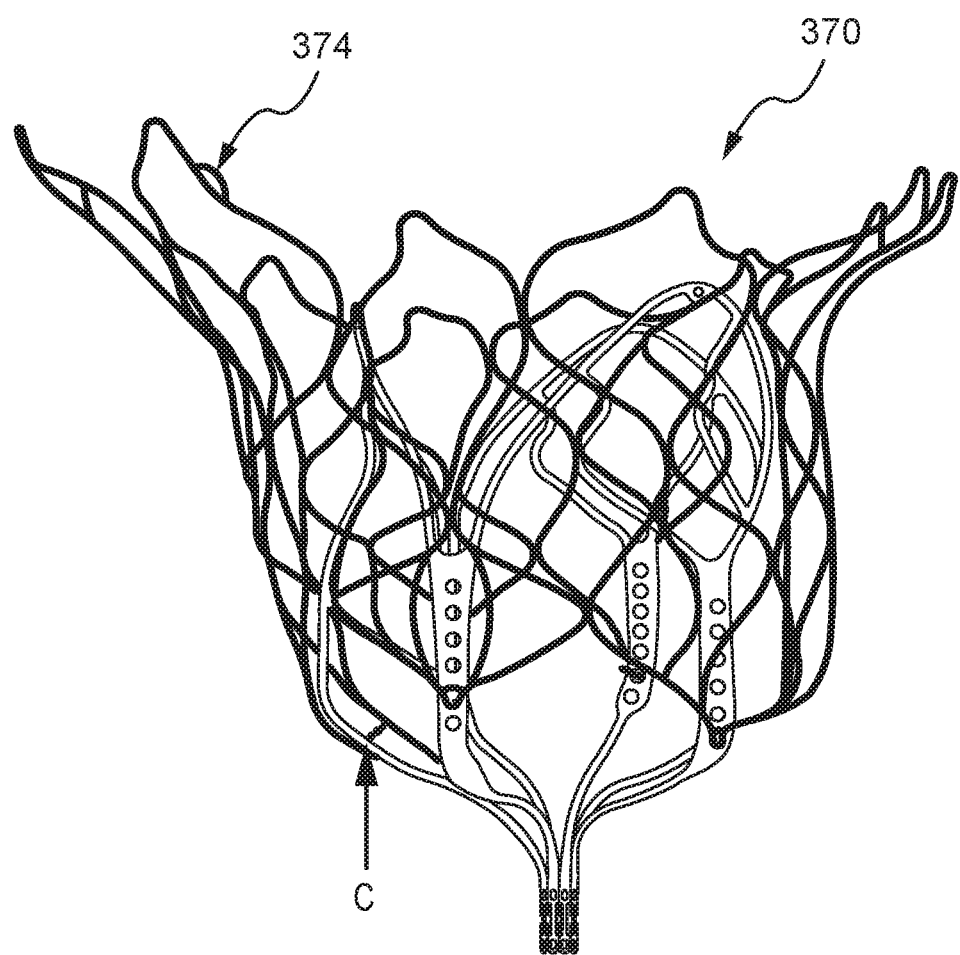
FIGS. 22-24 are side, front, and top views of an assembly of the inner wireframe structure of FIGS. 16-18 and the outer frame of FIGS. 19-21, forming a support structure for a prosthetic valve, according to an embodiment.
Figure 23:
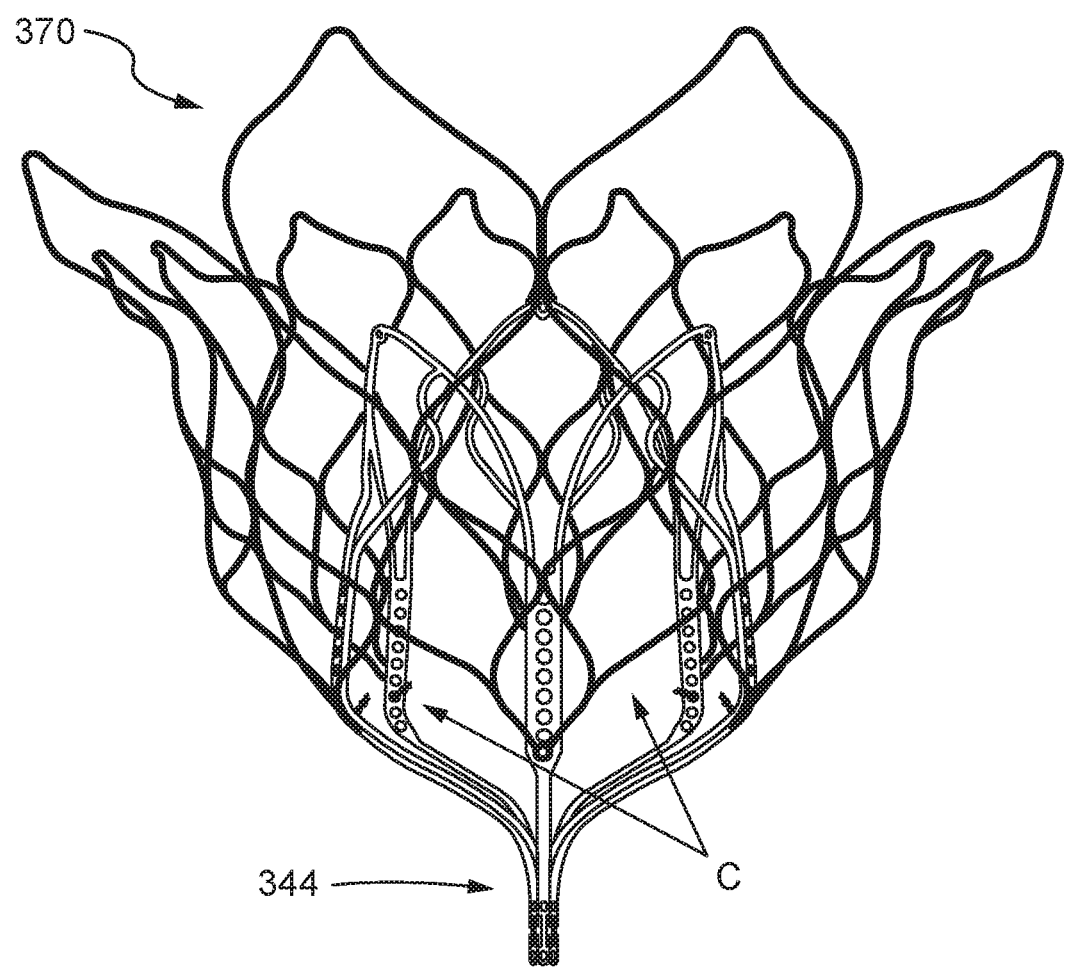
Figure 24:
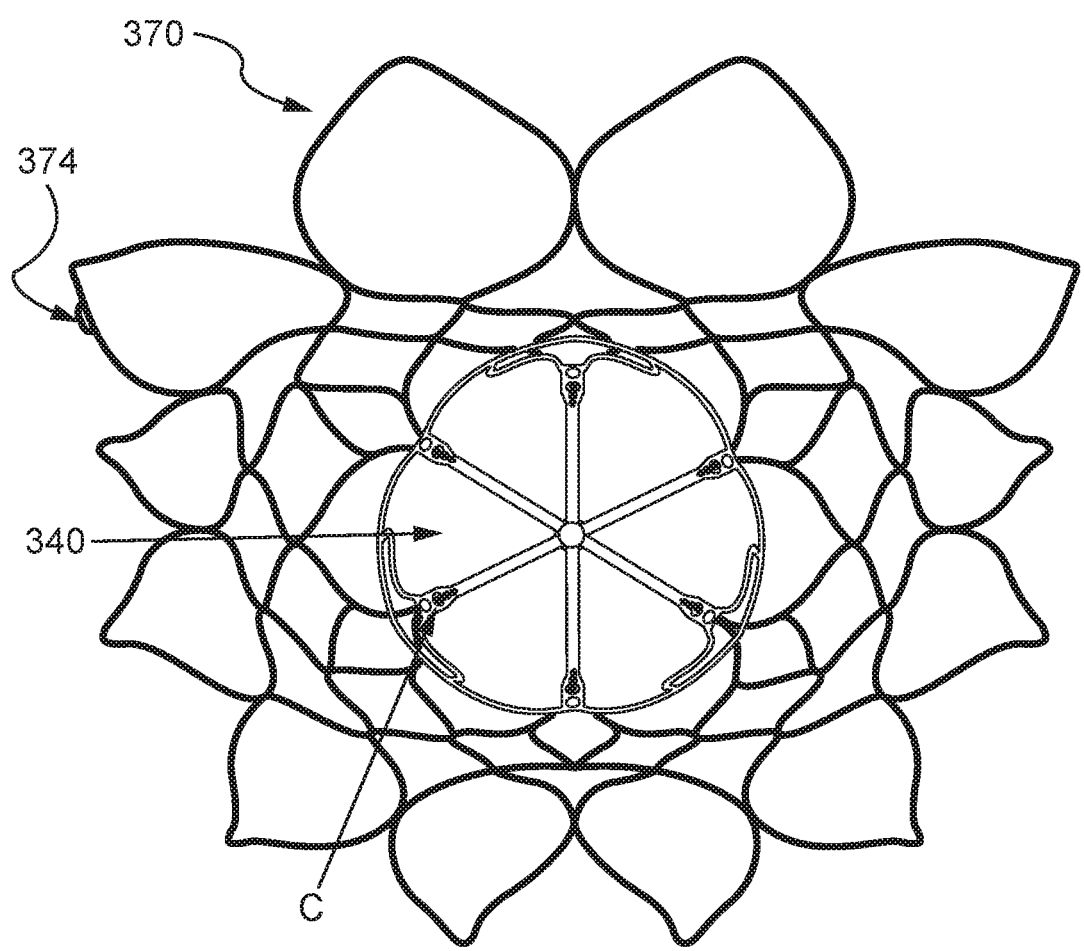

Outer frame 370 and inner frame 340 are shown coupled together in FIGS. 22-24, in front, side, and top views, respectively. The two frames collectively form a structural support for a prosthetic valve such as valve 10" in FIG. 15. The frames support the valve leaflet structure in the desired relationship to the native valve annulus, support the coverings for the two frames to provide a barrier to blood leakage between the atrium and ventricle, and couple to the tether (by the inner frame 340) to aid in holding the prosthetic valve in place in the native valve annulus by the tether connection to the ventricle wall. The two frames are connected at six coupling points (representative points are identified as "C"). In this embodiment, the coupling points are implemented with a mechanical fastener, such as a short length of wire, passed through aperture (such as aperture 371A) in coupling portion 371 of outer frame 370 and corresponding openings in longitudinal posts (such as poste 342A) in body portion 342 of inner frame 340. Inner frame structure 340 is thus disposed within the outer frame 370 and secured coupled to it.

While various embodiments have been described above, it should be understood that they have been presented by way of example only, and not limitation, and as such, various changes in form and/or detail may be made. Any portion of the apparatus and/or methods described herein may be combined in any suitable combination, unless explicitly expressed otherwise. Where methods and/or schematics described above indicate certain events occurring in certain order, the ordering of certain events and/or flow patterns may be modified. Additionally, certain events may be performed concurrently in parallel processes when possible, as well as performed sequentially.

What is claimed:

1. A method of manufacturing a prosthetic heart valve, comprising:
    forming an outer frame of a shape memory alloy;
    forming an inner frame of a shape memory alloy, the inner frame having a first portion and a second portion;
    coupling the outer frame to the inner frame;
    coupling a prosthetic leaflet assembly to the first portion of the inner frame; and
    compressing the second portion of the inner frame over a first end of a tether.

2. The method of claim 1, wherein the shape memory alloy of the outer frame is a nickel-titanium alloy.

3. The method of claim 1, wherein the shape memory alloy of the inner frame is a nickel-titanium alloy.

4. The method of claim 1, wherein the outer frame is coupled to the inner frame by one or more mechanical fasteners.

5. The method of claim 1, wherein the outer frame is formed separately from the inner frame.

6. The method of claim 1, wherein after coupling the outer frame to the inner frame, a distal end of the outer frame is disposed distal to a distal end of the inner frame.

7. The method of claim 1, wherein the inner frame is formed into an initial shape, and the first portion of the inner frame is expanded from the initial shape,
wherein compressing the second portion of the inner frame includes compressing the second portion of the inner frame from the initial shape.

8. The method of claim 7, wherein after compressing the second portion of the inner frame, the second portion of the inner frame defines a lumen having a width and a length that is greater than the width.

9. The method of claim 1, wherein after compressing the second portion of the inner frame over the first end of the tether, the second portion of the inner frame is disposed circumferentially continuously around the first end of the tether.

10. The method of claim 1, wherein the inner frame defines a central axis, and after compressing the second portion of the inner frame over the first end of the tether, the second portion of the inner frame is disposed along the central axis.

11. The method of claim 1, wherein forming the inner frame includes forming the second portion of the inner frame to include a plurality of "V"-shaped strut members, and compressing the second portion of the inner frame includes causing vertices of adjacent "V'-shaped strut members to move closer together longitudinally, and causing open ends of individual ones of the "V" shaped strut members to move closer together circumferentially.

12. The method of claim 1, wherein compressing the second portion of the inner frame over the first end of the tether includes compressing the second portion of the inner frame directly onto the first end of the tether.

13. The method of claim 1, wherein compressing the second portion of the inner frame over the first end of the tether includes compressing the second portion of the inner frame onto an intermediate structure between the second portion of the inner frame and the first end of the tether.

14. The method of claim 13, wherein the intermediate structure is a polymer or metal piece.

15. The method of claim 1, further comprising additionally coupling the second portion of the inner frame to the first end of the tether by a mechanical connection.

16. The method of claim 15, wherein the mechanical connection includes sutures.

17. The method of claim 15, wherein the mechanical connection includes pins.

18. The method of claim 1, further comprising additionally coupling the second portion of the inner frame to the first end of the tether by an adhesive.

19. The method of claim 1, wherein the inner frame is formed from a tube of the shape memory alloy.

20. The method of claim 1, wherein the outer frame is formed from a tube of the shape memory alloy.

* * * * *